United States Patent
Zhang

(10) Patent No.: US 11,566,110 B2
(45) Date of Patent: Jan. 31, 2023

(54) SELF-ASSEMBLED AMINO ACID SUPRAMOLECULAR POLYMER, PREPARATION THEREFOR, AND APPLICATION THEREOF

(71) Applicant: SUZHOU OULIT BIOPHARM CO., LTD, Jiangsu (CN)

(72) Inventor: Jian Zhang, Suzhou (CN)

(73) Assignee: SUZHOU OULIT BIOPHARM CO., LTD, Jiangsu (CN)

( * ) Notice: Subject to any disclaimer, the term of this patent is extended or adjusted under 35 U.S.C. 154(b) by 55 days.

(21) Appl. No.: 16/972,461

(22) PCT Filed: Jun. 3, 2019

(86) PCT No.: PCT/CN2019/089816
§ 371 (c)(1),
(2) Date: Dec. 4, 2020

(87) PCT Pub. No.: WO2019/233375
PCT Pub. Date: Dec. 12, 2019

(65) Prior Publication Data
US 2022/0073683 A1 Mar. 10, 2022

(30) Foreign Application Priority Data

Jun. 4, 2018 (CN) .......................... 201810562174.5
Jun. 4, 2018 (CN) .......................... 201810562197.6
Jun. 4, 2018 (CN) .......................... 201810562220.1

(51) Int. Cl.
*C08G 83/00* (2006.01)
*A61K 8/9789* (2017.01)
(Continued)

(52) U.S. Cl.
CPC .......... *C08G 83/008* (2013.01); *A61K 8/0216* (2013.01); *A61K 8/19* (2013.01);
(Continued)

(58) Field of Classification Search
CPC ....... C11D 3/0015; C11D 3/33; C11D 3/3719; C11D 3/50; C11D 17/0021; C11D 17/06;
(Continued)

(56) References Cited

U.S. PATENT DOCUMENTS

| | | |
|---|---|---|
| 6,090,250 A | 7/2000 | Mazzeo et al. |
| 8,697,614 B2 | 4/2014 | Choban et al. |
| 2012/0035108 A1 | 2/2012 | Miyamoto et al. |

FOREIGN PATENT DOCUMENTS

| | | |
|---|---|---|
| CN | 1798821 A | 7/2006 |
| CN | 103126921 A | 6/2013 |

(Continued)

OTHER PUBLICATIONS

JP07188694 A machine translation (Hattori Tatsuya; Sano Keigo; Yoshihara Hideki) 1995(patent).[online][retrieved on Sep. 18, 2022]. Retrieved from Espacenet (https://worldwide.espacenet.com/patent/search/family/018284140/publication/JPH07188694A?q=JP3296062) (Year: 1995) (Year: 1995).*

(Continued)

*Primary Examiner* — Adam C Milligan
*Assistant Examiner* — Amanda Michelle Petritsch
(74) *Attorney, Agent, or Firm* — Medler Ferro Woodhouse Mills PLLC

(57) ABSTRACT

Provided are a self-assembled amino acid supramolecular polymer and a preparation method therefor. Further provided is an application of the self-assembled amino acid supramolecular polymer in the fields of daily chemical, agricultural, and pharmaceutical industries. The provided self-assembled amino acid supramolecular polymer has good performance, and has obvious effects in aspects such as bacteriostasis, pesticide removal, and odor elimination. The provided self-assembled amino acid supramolecular polymer is applicable to toothpastes, skin care compositions, (Continued)

laundry detergents, soaps, washing powders, detergents, masks, etc.

18 Claims, 26 Drawing Sheets

(51) Int. Cl.
| | |
|---|---|
| A61K 8/02 | (2006.01) |
| A61K 8/19 | (2006.01) |
| A61K 8/34 | (2006.01) |
| A61K 8/42 | (2006.01) |
| A61K 8/49 | (2006.01) |
| A61K 8/86 | (2006.01) |
| A61K 8/88 | (2006.01) |
| A61K 8/92 | (2006.01) |
| A61Q 11/00 | (2006.01) |
| A61Q 19/10 | (2006.01) |
| C11D 3/00 | (2006.01) |
| C11D 3/33 | (2006.01) |
| C11D 3/37 | (2006.01) |
| C11D 3/50 | (2006.01) |
| C11D 17/00 | (2006.01) |
| C11D 17/06 | (2006.01) |
| A61K 8/9717 | (2017.01) |

(52) U.S. Cl.
CPC ............ *A61K 8/345* (2013.01); *A61K 8/42* (2013.01); *A61K 8/49* (2013.01); *A61K 8/86* (2013.01); *A61K 8/88* (2013.01); *A61K 8/922* (2013.01); *A61K 8/925* (2013.01); *A61K 8/9717* (2017.08); *A61K 8/9789* (2017.08); *A61Q 11/00* (2013.01); *A61Q 19/10* (2013.01); *C11D 3/0015* (2013.01); *C11D 3/33* (2013.01); *C11D 3/3719* (2013.01); *C11D 3/50* (2013.01); *C11D 17/0021* (2013.01); *C11D 17/06* (2013.01); *A61K 2800/10* (2013.01); *A61K 2800/30* (2013.01); *A61K 2800/412* (2013.01); *A61K 2800/48* (2013.01); *A61K 2800/524* (2013.01); *A61K 2800/92* (2013.01)

(58) Field of Classification Search
CPC .... C08G 83/008; C08G 69/10; C07C 233/47; C07C 231/02; C07B 2200/13; A61Q 11/00; A61Q 19/10; A61Q 19/00; A61K 8/0216; A61K 8/19; A61K 8/345; A61K 8/42; A61K 8/49; A61K 8/86; A61K 8/88; A61K 8/922; A61K 8/925; A61K 8/9717; A61K 8/9789; A61K 2800/10; A61K 2800/30; A61K 2800/412; A61K 2800/48; A61K 2800/524; A61K 2800/92; A61K 8/0212; A61K 2800/413; A61K 8/04; A61K 8/24; A61K 8/25; A61K 8/26; A61K 8/27; A61K 8/29; A61K 8/44
See application file for complete search history.

(56) References Cited

FOREIGN PATENT DOCUMENTS

| | | | | |
|---|---|---|---|---|
| CN | 103130675 | A | | 6/2013 |
| CN | 106118914 | A | | 11/2016 |
| CN | 107260563 | A | | 10/2017 |
| CN | 108451783 | A | | 8/2018 |
| CN | 108653025 | A | | 10/2018 |
| CN | 108752228 | A | | 11/2018 |
| CN | 108752420 | A | | 11/2018 |
| EP | 1609836 | | | 12/2005 |
| EP | 2319894 | | | 5/2011 |
| JP | 07188694 | A | * | 7/1995 |
| JP | H07-188694 | A | | 7/1995 |
| JP | 11349932 | A | * | 12/1999 |
| JP | 2004331568 | A | * | 11/2004 ............... A61K 8/55 |
| JP | 2008303183 | A | * | 12/2008 |
| WO | WO-9920237 | A1 | * | 4/1999 ............ A61K 33/42 |
| WO | 2018/006734 | | | 1/2018 |

OTHER PUBLICATIONS

Bhattachary et al., "First Report of Phase Selective Gelation of Oil from Oil/Water Mixtures. Possible Implications toward Containing Oil Spills," Chem. Commun. 185-186 (2001), DOI: 10.1039/b007848o.

Liu et al., "Research situation for phase-selective supramolecular oil gelators," Petrochemical Technology 43(12):1464-1472 (2014).

Pal et al., "Molecular mechanism of physical gelation of hydrocarbons by fatty acid amides of natural amino acids," Tetrahedron 63(31):7334-7348 (2007).

English Translation of the International Search Report in PCT/CN2019/089816, dated Sep. 2, 2019.

English Translation of the International Search Report in PCT/CN2019/089819, dated Sep. 2, 2019.

Restriction Requirement in U.S. Appl. No. 16/972,465, dated Mar. 31, 2022.

Sivaramakrishna et al., "Self-assembly, supramolecular organization, and phase transitions of a homologous series of N-acyl-L-alanines (n=8-20)," Colloids and Surfaces A: Physiochem Eng Aspects 471:108-116 (2015).

Radley and Tracey, "A Laser Diffraction and Nuclear Magnetic Resonance Investigation of the Cholesteric Potassium N-dodecanoylalaninate Mesophase System," Canadian Journal of Chemistry 63(1):95-99 (1985).

Luo et al., Self-assembled Organogels Formed by Mono-chain L-alanine Derivatives, Chemical Communications (17):1556-1557 (2001).

Non-Final Office Action issued in U.S. Appl. No. 16/972,465, dated May 26, 2022.

* cited by examiner

Data File C:\HPCHEM1\DATA\160307\03070202.D                                    Sample Name: N-YGX-L-BAS
===============================================================================

Injection Date    : 3/7/2016 6:13:21 AM              Seq. Line :      2
Sample Name       : N-YGX-L-BAS                      Location  :  Vial 2
Acq. Operator     : gxq                              Inj       :      1
Acq. Instrument   : Instrument 1                     Inj Volume:   20 μl
Acq. Method       : E:\1\METHODS\LC-WM5W.M
Last changed      : 3/7/2016 5:16:21 AM by gxq
Analysis Method   : E:\1\METHODS\WM5W.M
Last changed      : 3/7/2016 8:31:12 PM by gxq
                    (modified after loading)

FIG. 5

Area Percent Report

Sorted By           : Signal
Multiplier          : 1.0000
Dilution            : 1.0000
Use Multiplier & Dilution Factor with ISTDs Signal 1: DAD1 B, Sig=210, 4 Ref=360, 4

| Peak # | RetTime [min] | Type | Width [min] | Area [mAU*s] | Height [mAU] | Area % |
|---|---|---|---|---|---|---|
| 1 | 2.541 | MM | 0.0651 | 1.83107 | 4.68540e-1 | 0.0197 |
| 2 | 11.533 | BB | 0.2755 | 32.12540 | 1.47861 | 0.3456 |
| 3 | 28.656 | BV | 0.4207 | 111.53594 | 3.26384 | 1.1997 |
| 4 | 29.753 | VB | 1.0723 | 9151.25977 | 124.39609 | 98.4350 |

Totals :  9296.75218   129.60708

\*\*\* End of Report \*\*\*

FIG. 5 (cont'd)

GPC Sample Results

|   | Retention Time | Mn | Mw | MP | Mz | Poly-dispersity |
|---|---|---|---|---|---|---|
| 1 | 12.804 | 34606 | 125841 | 111225 | 278604 | 3.636 |

Mp: 111225 Name: Peak3

|    | RT     | Mol Wt | Log Mol Wt | Area | Cumulative % |
|----|--------|--------|------------|------|--------------|
| 1  | 10.868 | 770427 | 5.886731   | 1751 | 3.016        |
| 2  | 10.936 | 711395 | 5.852111   | 3604 | 3.451        |
| 3  | 11.005 | 657543 | 5.817924   | 3867 | 3.918        |
| 4  | 11.073 | 608364 | 5.784164   | 4172 | 4.420        |
| 5  | 11.141 | 563406 | 5.750822   | 4461 | 4.958        |
| 6  | 11.209 | 522265 | 5.717891   | 4776 | 5.533        |
| 7  | 11.277 | 484577 | 5.685363   | 5159 | 6.159        |
| 8  | 11.345 | 450019 | 5.653231   | 5594 | 6.835        |
| 9  | 11.414 | 418299 | 5.621487   | 6051 | 7.565        |
| 10 | 11.482 | 389156 | 5.590123   | 6566 | 8.358        |
| 11 | 11.550 | 362353 | 5.559132   | 7106 | 9.214        |
| 12 | 11.618 | 337681 | 5.528506   | 7695 | 10.143       |
| 13 | 11.686 | 314947 | 5.498238   | 8313 | 11.146       |
| 14 | 11.754 | 293981 | 5.468319   | 8977 | 12.231       |
| 15 | 11.823 | 274626 | 5.438742   | 9707 | 13.402       |

FIG. 13 (cont'd)

Mp: 111225 Name: Peak3

|  | RT | Mol Wt | Log Mol Wt | Area | Cumulative % |
|---|---|---|---|---|---|
| 16 | 11.891 | 256744 | 5.409500 | 10472 | 14.670 |
| 17 | 11.959 | 240206 | 5.380584 | 11250 | 16.028 |
| 18 | 12.027 | 224899 | 5.351988 | 12044 | 17.482 |
| 19 | 12.095 | 210718 | 5.323702 | 12856 | 19.033 |
| 20 | 12.163 | 197570 | 5.295721 | 13661 | 20.683 |
| 21 | 12.231 | 185388 | 5.268036 | 14477 | 22.429 |
| 22 | 12.300 | 174036 | 5.240639 | 15282 | 24.269 |
| 23 | 12.368 | 163502 | 5.213523 | 16047 | 26.206 |
| 24 | 12.436 | 153702 | 5.186681 | 16721 | 28.220 |
| 25 | 12.504 | 144578 | 5.160103 | 17314 | 30.303 |
| 26 | 12.572 | 136077 | 5.133784 | 17786 | 32.442 |
| 27 | 12.640 | 128149 | 5.107715 | 18170 | 34.626 |
| 28 | 12.709 | 120750 | 5.081888 | 18483 | 36.846 |
| 29 | 12.777 | 113841 | 5.056297 | 18615 | 39.076 |
| 30 | 12.845 | 107362 | 5.030932 | 18615 | 41.308 |
| 31 | 12.913 | 101342 | 5.005788 | 18556 | 43.529 |
| 32 | 12.981 | 95687 | 4.980855 | 18373 | 45.731 |
| 33 | 13.049 | 90391 | 4.956126 | 18117 | 47.899 |
| 34 | 13.118 | 85427 | 4.931594 | 17792 | 50.026 |
| 35 | 13.186 | 80770 | 4.907251 | 17382 | 52.105 |

FIG. 13 (cont'd)

Mp: 111225 Name: Peak3

|    | RT     | Mol Wt | Log Mol Wt | Area  | Cumulative % |
|----|--------|--------|------------|-------|--------------|
| 36 | 13.254 | 76399  | 4.883090   | 17009 | 54.139       |
| 37 | 13.322 | 72294  | 4.859102   | 16605 | 56.124       |
| 38 | 13.390 | 68435  | 4.835280   | 16143 | 58.051       |
| 39 | 13.458 | 64806  | 4.811616   | 15655 | 59.919       |
| 40 | 13.527 | 61391  | 4.788103   | 15122 | 61.721       |
| 41 | 13.595 | 58175  | 4.764734   | 14548 | 63.452       |
| 42 | 13.663 | 55144  | 4.741499   | 13916 | 65.111       |
| 43 | 13.731 | 52287  | 4.718393   | 13280 | 66.695       |
| 44 | 13.799 | 49591  | 4.695406   | 12607 | 68.197       |
| 45 | 13.867 | 47047  | 4.672532   | 11912 | 69.614       |
| 46 | 13.936 | 44644  | 4.649763   | 11200 | 70.946       |
| 47 | 14.004 | 42373  | 4.627090   | 10460 | 72.191       |
| 48 | 14.072 | 40226  | 4.604508   | 9715  | 73.346       |
| 49 | 14.140 | 38195  | 4.582007   | 8993  | 74.414       |
| 50 | 14.208 | 36273  | 4.559580   | 8308  | 75.397       |
| 51 | 14.276 | 34452  | 4.537220   | 7699  | 76.310       |
| 52 | 14.345 | 32728  | 4.514918   | 7216  | 77.169       |
| 53 | 14.413 | 31093  | 4.492668   | 6811  | 77.979       |
| 54 | 14.481 | 29543  | 4.47062    | 6528  | 78.758       |
| 55 | 14.549 | 28073  | 4.448291   | 6351  | 79.517       |

FIG. 13 (cont'd)

Mp: 111225 Name: Peak3

| | RT | Mol Wt | Log Mol Wt | Area | Cumulative % |
|---|---|---|---|---|---|
| 56 | 14.617 | 26678 | 4.426149 | 6233 | 80.264 |
| 57 | 14.685 | 25353 | 4.404027 | 6212 | 81.007 |
| 58 | 14.754 | 24094 | 4.381918 | 6263 | 81.754 |
| 59 | 14.822 | 22899 | 4.359814 | 6307 | 82.510 |
| 60 | 14.890 | 21762 | 4.337708 | 6359 | 83.273 |
| 61 | 14.958 | 20682 | 4.315592 | 6433 | 84.046 |
| 62 | 15.026 | 19654 | 4.293458 | 6505 | 84.827 |
| 63 | 15.094 | 18677 | 4.271299 | 6572 | 85.613 |
| 64 | 15.163 | 17746 | 4.249107 | 6561 | 86.394 |
| 65 | 15.231 | 16861 | 4.226874 | 6531 | 87.178 |
| 66 | 15.299 | 16017 | 4.204593 | 6505 | 87.954 |
| 67 | 15.367 | 15214 | 4.182257 | 6411 | 88.718 |
| 68 | 15.435 | 14450 | 4.159856 | 6287 | 89.473 |
| 69 | 15.503 | 13721 | 4.137384 | 6128 | 90.205 |
| 70 | 15.572 | 13027 | 4.114833 | 5927 | 90.913 |
| 71 | 15.640 | 12365 | 4.092196 | 5700 | 91.593 |
| 72 | 15.708 | 11735 | 4.069465 | 5421 | 92.240 |
| 73 | 15.776 | 11133 | 4.046631 | 5135 | 92.852 |
| 74 | 15.844 | 10561 | 4.023688 | 4847 | 93.426 |

FIG. 13 (cont'd)

Mp: 111225 Name: Peak3

|    | RT     | Mol Wt | Log Mol Wt | Area | Cumulative % |
|----|--------|--------|------------|------|--------------|
| 75 | 15.912 | 10014  | 4.000628   | 4537 | 93.967       |
| 76 | 15.981 | 9494   | 3.977443   | 4250 | 94.469       |
| 77 | 16.049 | 8998   | 3.954126   | 4019 | 94.948       |
| 78 | 16.117 | 8524   | 3.930668   | 3786 | 95.393       |
| 79 | 16.185 | 8074   | 3.907063   | 3533 | 95.813       |
| 80 | 16.253 | 7644   | 3.883302   | 3297 | 96.202       |
| 81 | 16.321 | 7234   | 3.859378   | 3045 | 96.564       |
| 82 | 16.390 | 6844   | 3.835284   | 2812 | 96.896       |
| 83 | 16.458 | 6472   | 3.811010   | 2621 | 97.206       |
| 84 | 16.526 | 6117   | 3.786551   | 2426 | 97.494       |
| 85 | 16.594 | 5780   | 3.761898   | 2235 | 97.759       |
| 86 | 16.662 | 5458   | 3.737044   | 2081 | 98.005       |
| 87 | 16.730 | 5152   | 3.711981   | 1936 | 98.234       |
| 88 | 16.799 | 4861   | 3.686701   | 1809 | 98.447       |
| 89 | 16.867 | 4583   | 3.661196   | 1705 | 98.651       |
| 90 | 16.935 | 4320   | 3.635460   | 1561 | 98.835       |
| 91 | 17.003 | 4069   | 3.609484   | 1409 | 99.000       |
| 92 | 17.071 | 3831   | 3.583261   | 1306 | 99.156       |
| 93 | 17.139 | 3604   | 3.556782   | 1214 | 99.300       |
| 94 | 17.208 | 3389   | 3.530042   | 1119 | 99.433       |

FIG. 13 (cont'd)

| 95 | 17.276 | 3184 | 3.503030 | 1094 | 99.564 |
| 96 | 17.344 | 2990 | 3.475741 | 1075 | 99.695 |
| 97 | 17.412 | 2807 | 3.448167 | 999 | 99.815 |
| 98 | 17.480 | 2632 | 3.420299 | 899 | 99.922 |
| 99 | 17.548 | 2467 | 3.392130 | 604 | 99.988 |
| 100 | 17.617 | 2310 | 3.363653 | 178 | 100.001 |

FIG. 13 (cont'd)

TEST REPORT

Report No : HWS201506169

Sample Name : Uraful amino acid toothpaste (mint flavor)

Producer : Suzhou Jinmao Daily Chemicals Co., Ltd.

Entrusting Party : Suzhou Weimei Biotechnology Co., Ltd.

KEY LABORATORIES OF TESTING OF GENERAL ADMINISTRATION OF QUALITY SUPERVISION, INSPECTION & QUARANTINE

INSPECTION & QUARANTINE COMPREHENSIVE TECHNOLOGY CENTER OF SUZHOU ENTRY-EXIT INSPECTION & QUARANTINE BUREAU

Page 1 of 3 pages

FIG. 14

KEY LABORATORIES OF TESTING OF GENERAL
ADMINISTRATION OF QUALITY SUPERVISION, INSPECTION & QUARANTINE

INSPECTION & QUARANTINE COMPREHENSIVE TECHNOLOGY
CENTER OF SUZHOU ENTRY-EXIT INSPECTION & QUARANTINE BUREAU

Test Report

Report No. HWS201506169
Date: 2015-11-10

| The following information is provided and confirmed by the client. | | | |
|---|---|---|---|
| Sample information | Sample name | Uraful amino acid toothpaste (mint flavor) | |
| | Batch number or production date | 20151022 | |
| | Shelf life or expiration date | 20181021 | |
| | Sample character | Blue paste | |
| | Specification | 135 g/tube | |
| | Number of samples | 7 tubes in substitute packages | |
| Client information | Producer | Suzhou Jinmao Daily Chemicals Co., Ltd. | |
| | Entrusting party | Suzhou Weimei Biotechnology Co., Ltd. | |
| The following description is provided by the laboratory. | | | |
| Test information | Test type | Entrusted test | |
| | Arrival date of sample(s) | 2015.11.03 | Test period | 2015.11.03-2015.11.10 |
| | Test standard | GB8372-2008 | |
| Test conclusion | The samples were subjected to organoleptic, physical-chemical and microbiological tests according to GB8372-2008. Under the testing conditions of the present laboratory, the test results show that: the tested items of the samples meet the requirements of GB8372-2008. | | |

AUTHORIZED SIGNATURE

\*\*\* End of the page\*\*\*

Note: The test report is only responsible for the samples tested. Any objection to the result(s) can be raised for re-inspection within 15 days from receiving the report. No partial copy of the report or misuse of the report for improper promotion will be allowed without the written consent of our laboratory.

Page 2 of 3 pages

FIG. 15

KEY LABORATORIES OF TESTING OF GENERAL
ADMINISTRATION OF QUALITY SUPERVISION, INSPECTION & QUARANTINE

INSPECTION & QUARANTINE COMPREHENSIVE TECHNOLOGY
CENTER OF SUZHOU ENTRY-EXIT INSPECTION & QUARANTINE BUREAU

Test Report

Report No. HWS201506169
Date: 2015-11-10

Test results (organoleptic)

| Item | Unit of test result | Technical requirements | Test result | Individual evaluation |
|---|---|---|---|---|
| Paste body | -- | Uniform; no foreign matter | Requirements satisfied | Qualified |
| Package appearance | -- | Cap and tube mouth are intimately fit; tube mouth is not damaged paste body does not leak. | Requirements satisfied | Qualified |

Test results (physical-chemical)

| Item | Unit of test result | Technical requirements | Test result | Individual evaluation |
|---|---|---|---|---|
| Lead (Pb) content | mg/kg | ≤ 15 | <5 | Qualified |
| Arsenic (As) content | mg/kg | ≤ 5 | <5.0 | Qualified |
| PH value | -- | 5.5-10.0 | 6.4 | Qualified |
| Stability | -- | No paste flows out of tube mouth; no liquid is separated; scent and color are normal. | Requirements satisfied | Qualified |
| Unduly hard particles | -- | No scratch on glass plate | Requirement satisfied | Qualified |
| Free fluorine | % | 0.05-0.15 (lower limit only applicable to fluorine-containing anticarious toothpaste) | <0.01 | Qualified |
| Total fluorine | -- | 0.05-0.15% (lower limit only applicable to fluorine-containing anticarious toothpaste) | Not detected | Qualified |

Test results (physical-chemical)

| Item | Unit of test result | Technical requirements | Test result | Individual evaluation |
|---|---|---|---|---|
| Total bacterial count | CFU/g | ≤500 | <10 | Qualified |
| Fecal coliform | -- | Undetectable | Not detected | Qualified |
| Pseudomonas aeruginosa | -- | Undetectable | Not detected | Qualified |
| Staphylococcus aureus | -- | Undetectable | Not detected | Qualified |
| Total count of moulds and saccharomyces | CFU/g | ≤100 | <10 | Qualified |

Note: When the measured total fluorine amount is lower than the concentration of 0.2 mg/kg measured by the method, the result is indicated as "not detected".

* End of the page*
* End of the page*

Note: The test report is only responsible for the samples tested. Any objection to the result(s) can be raised for re-inspection within 15 days from receiving the report. No partial copy of the report or misuse of the report for improper promotion will be allowed without the written consent of our laboratory Page 3 of 3 pages

FIG. 16

No: (19) WPHG0523

Collection of Test Results

Page 2 of 2

| No. | Test Item | Unit | Technical requirement | Test result | Individual judge |
|---|---|---|---|---|---|
| | Detergent power | — | ≥ detergent power of standard laundry liquid | The samples have a higher detergent power on JB01, JB02, and JB03 dirty cloth than the detergent power of the standard laundry liquid on JB01, JB02, JB03 dirty cloth. | Qualified |
| Note | | | | | |

(Only responsible for the submitted samples)

FIG. 19

SELF-ASSEMBLED AMINO ACID SUPRAMOLECULAR POLYMER, PREPARATION THEREFOR, AND APPLICATION THEREOF

TECHNICAL FIELD

The present disclosure pertains to the technical field of preparation of amino acid type surfactants, and particularly relates to a self-assembled amino acid supramolecular polymer and its preparation and application.

BACKGROUND ART

Surfactants are indispensable for many fields such as daily chemical industry, agriculture, pharmaceutical industry, etc. There are dozens of surfactants currently used in the market, but the main surfactants that are commonly used include sodium dodecylbenzene sulfonate (SLS), sodium laureth sulfate (AES) and sodium lauryl sulfate (K12). While these three major surfactants have been used for decades or even over a hundred years, their negative effects in use have gradually emerged, and their impact on human safety and the environment is frequently reported.

Among other surfactants, there may be mentioned, for example, sugar alkyl glycosides (APG), and amino acid surfactants, such as lauroyl-L-glutamic acid, lauroyl glycine, lauroyl sarcosine and the like. They are biomass based surfactants with high safety, good biodegradability and excellent skin feel, and thus have attracted more and more attention. However, because of the poor detergent power of this type of surfactants, they are rarely used alone as primary surfactants; instead, they often need to be used in conjunction with other primary surfactants. Hence, the troublesome problems caused by the primary surfactants used as daily chemicals in terms of safety and biodegradability haven't been solved fundamentally.

As a surfactant, pure N-lauroyl-L-alanine exhibits good wettability, foamability, antibacterial property, corrosion resistance, and antistatic property. It's substantially non-toxic and harmless, and it's also mild to skin. Its degradation products are an amino acid and a fatty acid which substantially have no influence on the environment. In addition, it has an advantage of good compatibility with other surfactants.

However, when N-lauroyl-L-alanine prepared by the prior art methods such as Schotten-Baumann condensation reaction is tested as a surfactant, it is found that its detergent power is not as high as anticipated theoretically. After a series of exploratory experimentations, the present inventors have discovered that the main reason for the low detergent power of N-lauroyl-L-alanine is the relatively high content of lauric acid in the N-lauroyl-L-alanine product prepared by this method. The presence of lauric acid prevents formation of a self-assembled polymer. The effect data of the sodium salt compound prepared from the N-lauroyl-L-alanine product are not as good as those obtained in the present disclosure. The high content of lauric acid leads to low product purity which seriously affects the quality of N-lauroyl-L-alanine. To remove the impurities, chromatography is entailed in addition to the original production process, so as to further purify the product. The operation is cumbersome and costly, and it is difficult to realize industrial production.

In view of the above facts, a method for preparing a self-assembled amino acid supramolecular polymer and application thereof are desirable. The N-lauroyl-L-alanine self-assembled polymer prepared by this method has a lauric acid content that is undetectable by HPLC and GC, and shows good decontamination effect. Additionally, the method involves a simple process and low cost, and it's easy to be industrialized.

SUMMARY

One object of the present disclosure is to provide a method for preparing a N-lauroyl-L-alanine self-assembled polymer and use of the N-lauroyl-L-alanine self-assembled polymer, wherein the prepared N-lauroyl-L-alanine self-assembled supramolecular polymer has good biodegradability and strong detergent power, very suitable for use in the daily chemical industry, agriculture, pharmaceutical industry and the like. As such, the defects of N-lauroyl-L-alanine prepared by the prior art, i.e. low purity and a high level of impurities, which seriously affect the quality of the product, are overcome.

The self-assembled amino acid supramolecular polymer according to the present disclosure has the following structure:

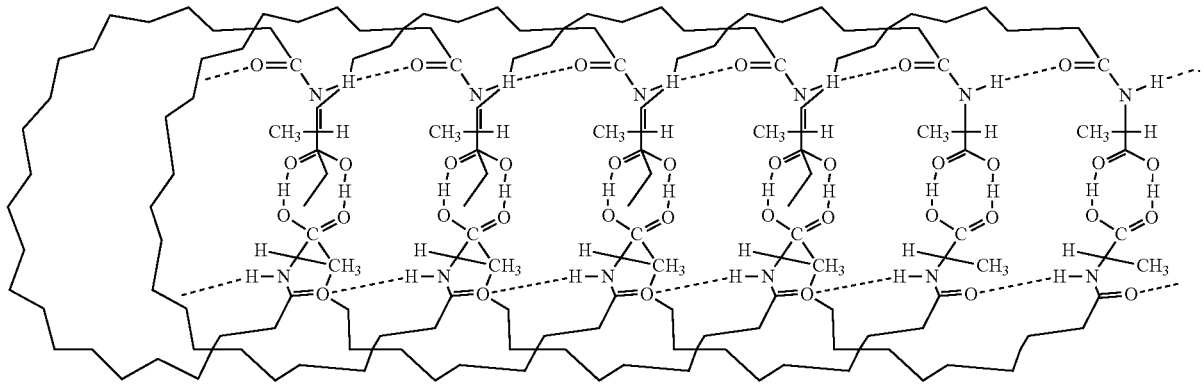

The self-assembled amino acid supramolecular polymer according to the present disclosure comprises N-lauroyl-L-alanine as a basic unit which self-assembles into a supramolecular polymer through hydrogen bonds, wherein the polymer is substantially free of lauric acid, wherein "substantially free" means that lauric acid is undetectable by HPLC and GC.

The self-assembled amino acid supramolecular polymer according to the present disclosure comprises N-lauroyl-L- alanine as a basic unit which self-assembles into a supramolecular polymer through hydrogen bonds, wherein the supramolecular polymer has a weight average molecular weight of between 2000 and 5,000,000.

The following technical solution is employed to achieve the object of the present disclosure and solve its technical problem. There is provided a method for preparing a self-assembled amino acid supramolecular polymer substantially free of lauric acid according to the present disclosure, comprising the following steps:

Adding a solvent, L-alanine and a catalyst to a crude N-lauroyl-L-alanine product, agitating under certain conditions, cooling, filtering, washing the resulting solid, and drying to obtain a N-lauroyl-L-alanine self-assembled polymer substantially free of lauric acid.

Preparation of the abovementioned crude N-lauroyl-L-alanine product includes the following steps:

(1) Dissolving L-alanine and a metallic inorganic base in a mixed solution of distilled water and an organic solvent, and stirring uniformly to obtain an L-alanine salt solution;

(2) Adding lauroyl chloride and a metallic inorganic base in sequence to the L-alanine salt solution obtained above, and then continuing the stirring under certain conditions to obtain a pasty N-lauroyl-L-alanine salt;

(3) Acidifying the pasty N-lauroyl-L-alanine salt obtained above to precipitate a white solid gradually, and then placing the resultant in an ice bath, filtering to obtain the crude N-lauroyl-L-alanine product.

In the aforementioned method, a molar ratio of the L-alanine to the metallic inorganic base in Step (1) is 1:(1-1.5).

In the aforementioned method, the metallic inorganic base in Step (1) is selected from one or more of sodium hydroxide, potassium hydroxide, sodium carbonate, and potassium carbonate.

In the aforementioned method, the organic solvent in Step (1) is selected from one or more of acetone, methanol, ethanol, acetonitrile, and tetrahydrofuran.

In the aforementioned method, a volume ratio of the distilled water to the organic solvent in Step (1) is 1:(1-1.5).

In the aforementioned method, a feeding molar ratio of the lauroyl chloride to the L-alanine in Step (2) is (0.8-1):1.

In the aforementioned method, the stirring conditions in Step (2) include: temperature 5-50° C., time 0.5-3.5 h.

In the aforementioned method, the metallic inorganic base in Step (2) has a concentration of 30-80%.

In the aforementioned method, the metallic inorganic base in Step (2) is selected from one or more of sodium hydroxide, potassium hydroxide, sodium carbonate, and potassium carbonate.

In the aforementioned method, the solvent in Step (4) is selected from one or more of acetone, methanol, ethanol, acetonitrile, tetrahydrofuran, and mixed solvents made from one or more of the above solvents with water.

In the aforementioned method, the catalyst in Step (4) is selected from one or more of sulfuric acid, p-toluenesulfonic acid, and emulsifiers.

In the aforementioned method, a molar ratio of the crude N-lauroyl-L-alanine product, the solvent, L-alanine, and the catalyst in Step (4) is 1:(5-10):(0.2-0.6): (0.001-0.2).

In the aforementioned method, the drying temperature in Step (4) is 40-70° C.

In the aforementioned method, the stirring conditions in Step (4) include: temperature 25-100° C., pressure 5 kg-50 kg, time 1-3 h.

The present disclosure further relates to a sodium salt of a self-assembled amino acid supramolecular polymer substantially free of lauric acid, and its structure is as follows:

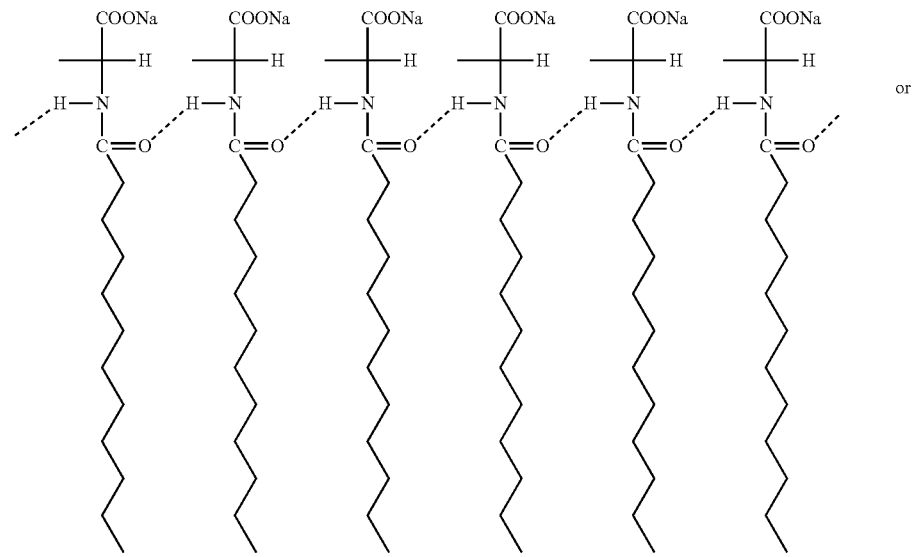

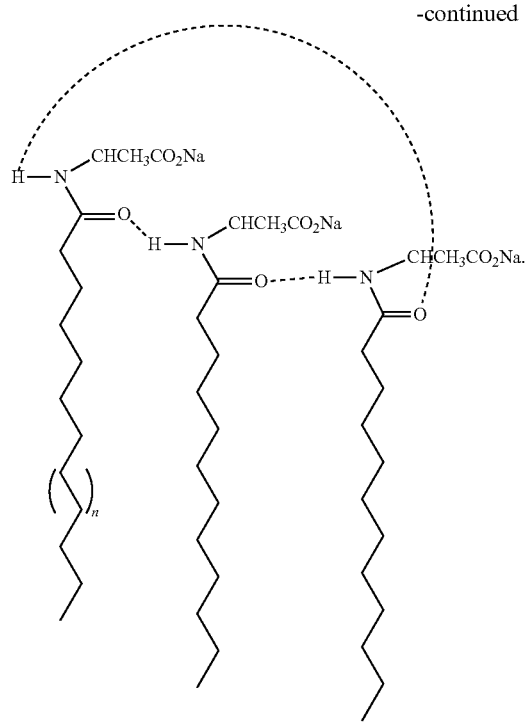

wherein n represents the number of sodium N-lauroyl-L-alanine molecules forming the self-assembled supramolecular polymer.

The present disclosure further discloses a sodium salt of a self-assembled amino acid supramolecular polymer, comprising sodium N-lauroyl-L-alanine as a basic unit which self-assembles into a supramolecular polymer through hydrogen bonds, wherein the supramolecular polymer has a weight average molecular weight of between 2800 and 770,000.

The following technical solution is further employed to achieve the object of the present disclosure and solve its technical problem. According to the present disclosure, there is provided use of the self-assembled amino acid supramolecular polymer obtained by the aforementioned preparation method as a surfactant used in the fields of daily chemicals, agriculture, and pharmaceutical industry.

The following technical solution is further employed to achieve the object of the present disclosure and solve its technical problem. According to the present disclosure, there is provided a supramolecular amino acid, wherein the supramolecular amino acid is formed by hydrogen bonding the N-lauroyl-L-alanine monomers obtained by the aforementioned preparation method.

The present disclosure has the following beneficial technical effects in comparison with the prior art:

1. The self-assembled amino acid supramolecular polymer according to the present disclosure is prepared by a method consisting of simple process steps. It is formed by condensation of natural lauric acid and natural L-alanine. It exists stably under ambient conditions, and is non-toxic and harmless to human body. Even if it enters human body, it will quickly degrade into lauric acid and L-alanine naturally, and the degradation products are natural materials that can be recycled. Furthermore, the reaction conditions are mild, and thus appropriate for industrial production.

2. The content of lauric acid in the self-assembled amino acid supramolecular polymer prepared by the method according to the present disclosure cannot be detected by HPLC or GC. Thus, the content of lauric acid has no influence on the structure or properties of N-lauroyl-L-alanine, thereby effectively avoiding the influence of lauric acid on product quality.

3. The self-assembled amino acid supramolecular polymer obtained by the method according to the present disclosure has a three-dimensional network structure which strongly facilitates adsorption of oil and other organics. In use, the pH is 6-7, which is more suitable for the pH requirement of human body. At least 90% of the polymer exists in the form of sodium salt, and the rest exists in the form of acid. They coexist in two dimensions and three dimensions, providing strong abilities for cleaning and for adsorption of bacteria, pesticides, odor, etc.

4. The self-assembled amino acid supramolecular polymer prepared by the method according to the present disclosure has a stable structure and stable properties, and it also possesses supramolecular properties. Due to the existence of various gelling factors in the solution containing the molecules, such as hydrogen bond, electrostatic force, hydrophobic force, and π-π interaction, the liquid components are driven to stand still. An amino acid having a three-dimensional network spatial structure is thus formed. As such, the polymer is imparted with the abilities for physical sterilization, odor removal, and pesticide residue removal. It has a sound bacteriostatic rate, and it is able to inhibit *Escherichia coli, Staphylococcus aureus* and *Candida albicans* each at a bacteriostatic rate up to 100%. It can remove pesticide residue effectively. The removal rate for methamidophos can reach 64.63%, and the removal rate for acephate can reach 74.66%. It also has good deodorizing performance.

5. The self-assembled amino acid supramolecular polymer prepared by the method according to the present disclosure exists in the form of countless columnar bodies with huge gaps between the molecules. The huge gaps can entrap organic substances such as drug molecules, pesticide residue and tiny inorganic particles. For applications in the pharmaceutical field, the self-assembled amino acid supramolecular polymer can encapsulate drug molecules, and act as a slow release agent, such that the active ingredients of a drug can be released slowly under the action of an enzyme. For applications in the pesticide field, the self-assembled amino acid supramolecular polymers can encapsulate a pesticide to prevent the pesticide from penetrating and entering the interior of a plant. For applications in the field of cosmetics, a combination of the self-assembled amino acid supramolecular polymer and a natural oil may modify the physical properties of the oil, such that the modified natural oil is close to the oil secreted by human body, and thus provides good experience to consumers. The self-assembled amino acid supramolecular polymer can encapsulate a cosmetic active material, so that the active material will not be easily oxidized or deactivated, and particles of the cosmetic active material can be dispersed uniformly and suspended in a cosmetic system.

GPC sample results: sample results

Retention Time: retention time

Mn: number average molecular weight

Mw: weight average molecular weight

Mz: higher average molecular weight

Mp: peak molecular weight

Figure 17:
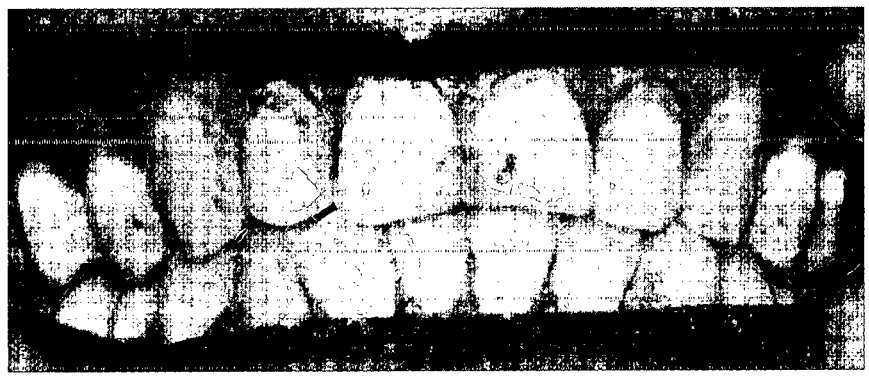
Figure 18:
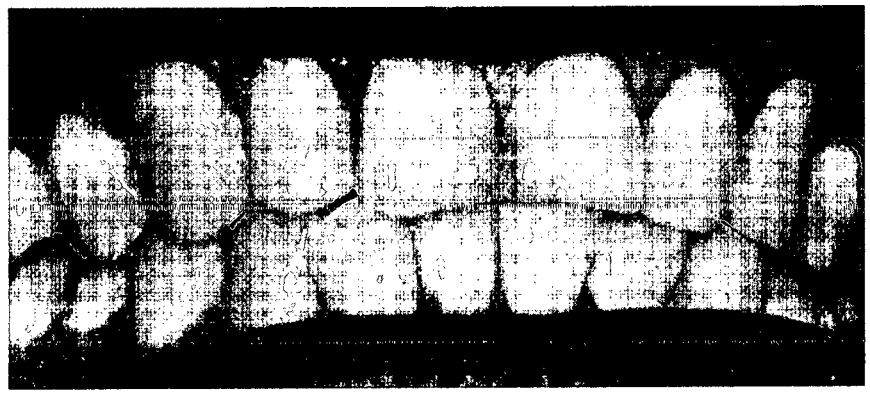
Figure 20:
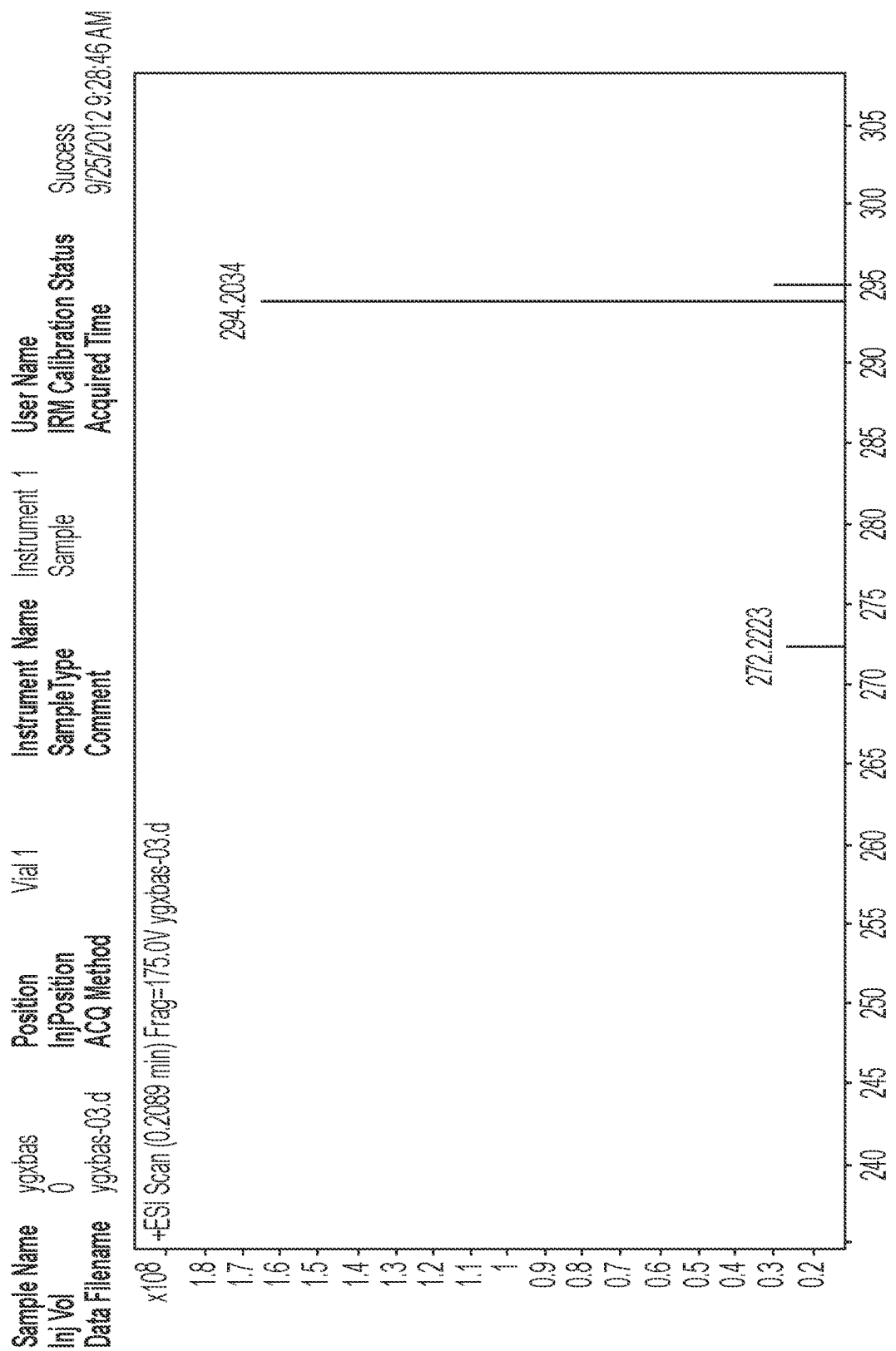

Polydispersity: indicating that the molecular weight is an average of the molecular weights of homologs;

FIGS. 14-16 are test reports of the amino acid toothpaste in Embodiment 3;

FIG. 17 shows a patient's teeth before cleaned with the amino acid toothpaste;

FIG. 18 shows the effect of cleaning the patient's teeth with the amino acid toothpaste;

FIG. 19 shows the test results of the detergent power of a laundry liquid;

FIG. 20 shows a mass spectrum of the self-assembled N-lauroyl-L-alanine polymer obtained according to the synthetic method in Embodiment 3 in the present disclosure.

DETAILED DESCRIPTION

After extensive and intensive research, the present inventors have discovered a peculiar method that can be used to form a polymer substantially free or free of lauric acid by self-assembly of N-lauroyl-L-alanine monomer via hydrogen bonding, and an elastic void-containing structure can be formed. This structure can immobilize oily substances. When the polymer forms a salt with a base, the resulting polymer salt may be used as a surfactant. The invention is accomplished on such a basis.

As used herein, "the polymer or its salt provided according to the present disclosure is substantially free or free of lauric acid" means that, for example, lauric acid cannot be detected by a high-performance liquid chromatograph (equipped with an ultraviolet detector; a chromatographic column: ODS-2HYPERSIL C18 250*4.6 mm 5 μm; a mobile phase vacuum filtration and degassing device; and a 0.45 μm organic filter membrane). That is, the content of lauric acid has no influence on the properties and structure of N-lauroyl-L-alanine, so that N-lauroyl-L-alanine can self-assemble into a supramolecular polymer by forming hydrogen bonds. Alternatively, it means that no molecular ion peak characteristic of lauric acid can be observed in the mass spectrum obtained by mass spectrometry, for example, without limitation, the mass spectrum obtained by an Agilent 1200/6220 LC/MS instrument, as shown in FIG. 20.

The N-lauroyl-L-alanine salts involved in the present disclosure are sodium N-lauroyl-L-alanine and/or potassium N-lauroyl-L-alanine. They may also be salts formed from N-lauroyl-L-alanine with basic amino acids, such as salts formed with arginine, histidine, lysine, and the like.

Polymer or Salts Thereof

There is provided a self-assembled amino acid supramolecular polymer or a salt thereof according to the present disclosure, wherein the polymer is formed by hydrogen bonding N-lauroyl-L-alanine monomers, wherein the polymer is substantially free or free of lauric acid.

Said hydrogen bonding N-lauroyl-L-alanine monomers may provide a structure as shown by Formula (I):

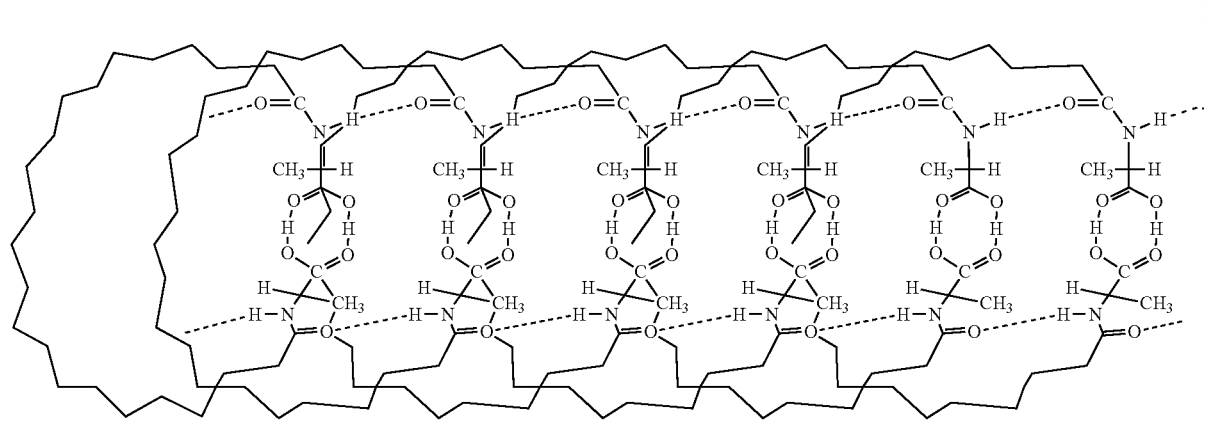

I

The self-assembled amino acid supramolecular polymer provided according to the present disclosure has a weight average molecular weight of between 2000 and 5,000,000, and a melting point of 82-84° C.

There is also provided a salt of the aforementioned self-assembled amino acid supramolecular polymer according to the present disclosure, wherein the salt is formed from the polymer with a base, wherein the base is selected from inorganic and organic bases.

In a preferred embodiment, the inorganic base is selected from sodium hydroxide, potassium hydroxide, or lithium hydroxide.

In a preferred embodiment, the organic base is a natural basic amino acid (arginine, lysine or histidine).

The sodium salt of the aforementioned self-assembled amino acid supramolecular polymer provided according to the present disclosure has a maximum solubility of 15w/v %, as measured according to a solubility measuring method (Chinese Pharmacopoeia (2015 edition), General Guide). That is, the maximum amount of the self-assembled polymeric sodium N-lauroyl-L-alanine dissolved in 100 ml water is 15 grams at 25° C. and 1 atm.

In one embodiment according to the present disclosure, there is provided a sodium salt of a self-assembled amino acid supramolecular polymer, formed by hydrogen bonding sodium N-lauroyl-L-alanine monomers, wherein the sodium salt of the polymer is substantially free or free of lauric acid.

Said hydrogen bonding sodium N-lauroyl-L-alanine monomers may provide a structure as shown by Formula (II):

hydrogen bonds and the first and last molecules are also linked by hydrogen bonds to form a columnar structure.

The sodium salt of the self-assembled amino acid supramolecular polymer provided according to the present disclosure has a weight average molecular weight of between 2,800-770,000, from which it can be inferred that n ranges from 10 to 3000; and the solubility of the sodium salt in water does not exceed 15 g/100 ml.

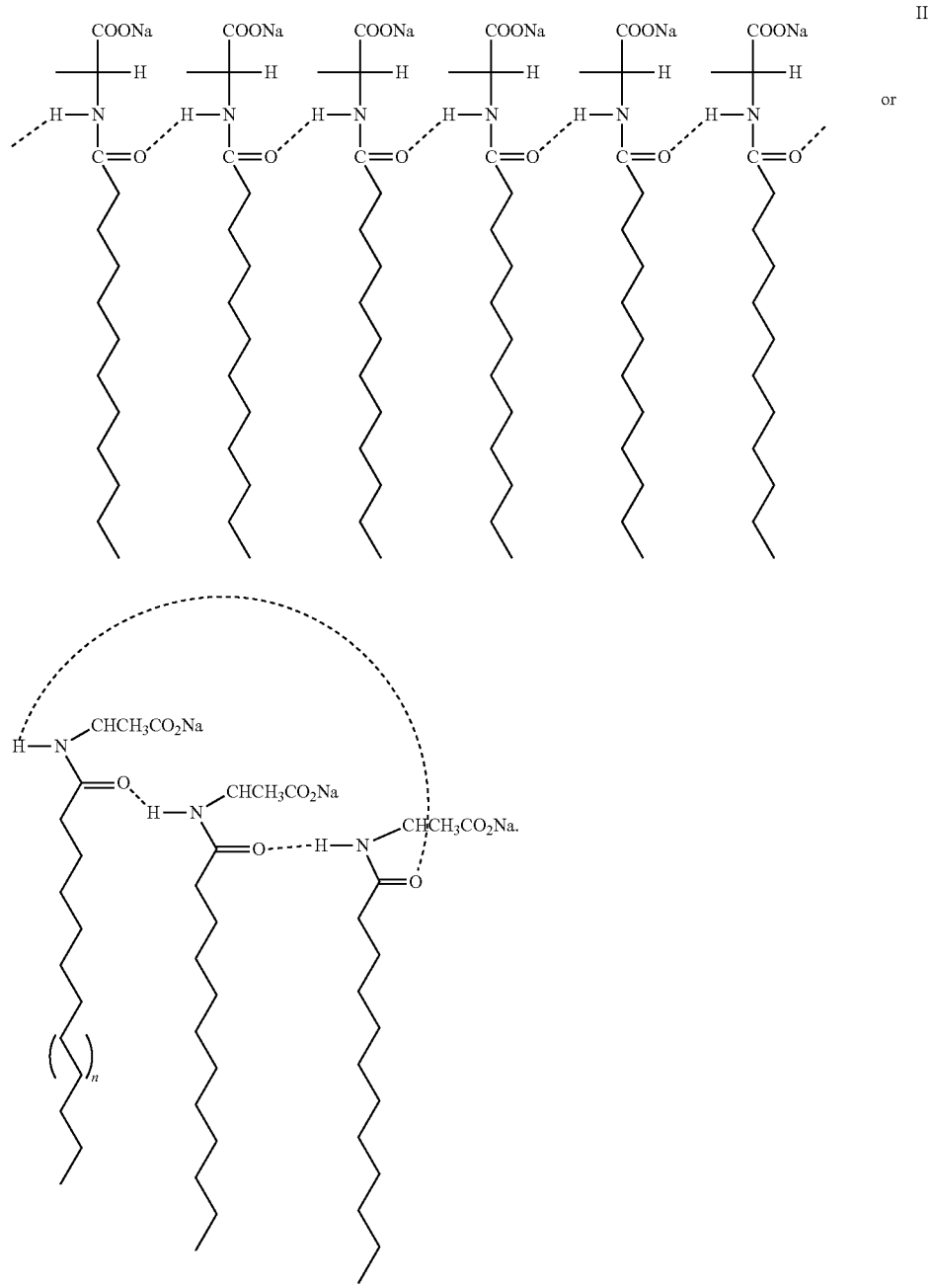

wherein n represents the number of sodium N-lauroyl-L-alanine molecules forming the self-assembled supramolecular polymer.

N sodium N-lauroyl-L-alanine molecules are linked in sequence by hydrogen bonds in the same plane, or n sodium N-lauroyl-L-alanine molecules are linked in sequence by According to the present disclosure, there is also provided a composition comprising the self-assembled amino acid supramolecular polymer or a salt thereof provided according to the present disclosure, and a polymer formed by hydrogen bonding N-lauroyl-L-alanyl-L-alanine monomers or a salt thereof, wherein the polymer formed by hydrogen bonding N-lauroyl-L-alanyl-L-alanine monomers or the salt thereof accounts for 0-40 wt. % based on the total weight of the composition.

Said hydrogen bonding N-lauroyl-L-alanyl-L-alanine monomers may provide a structure as shown by Formula (I'):

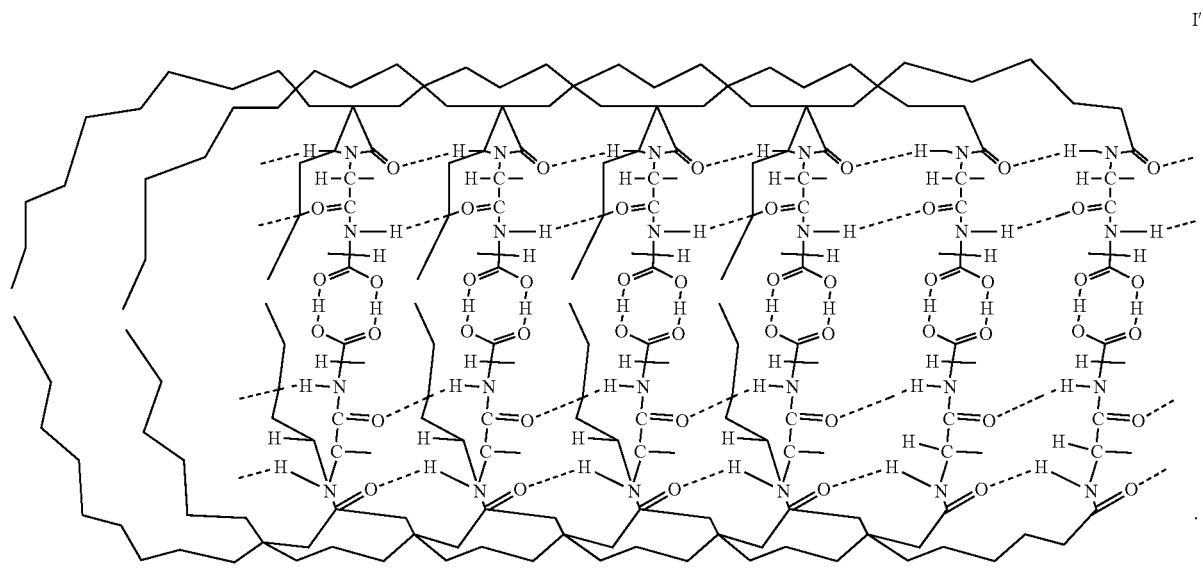

I' wherein the resulting polymer has a weight average molecular weight of between 5,000 and 5,000,000, and a melting point of 148-150° C.

Hydrogen bonding sodium N-lauroyl-L-alanyl-L-alanine monomers may further provide a structure as shown by Formula (II'):

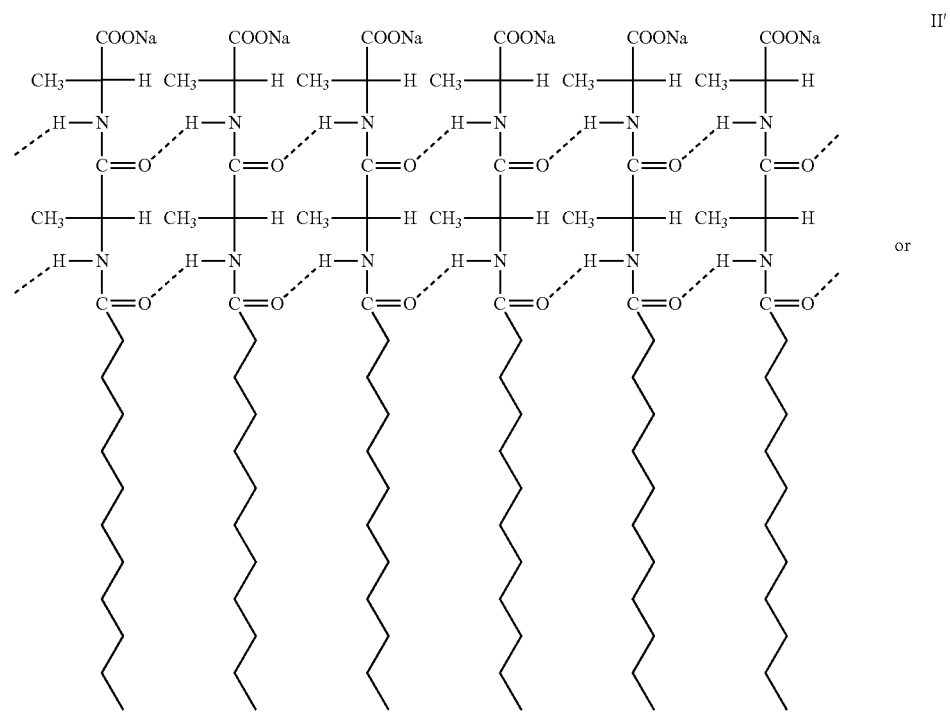

II' or

-continued

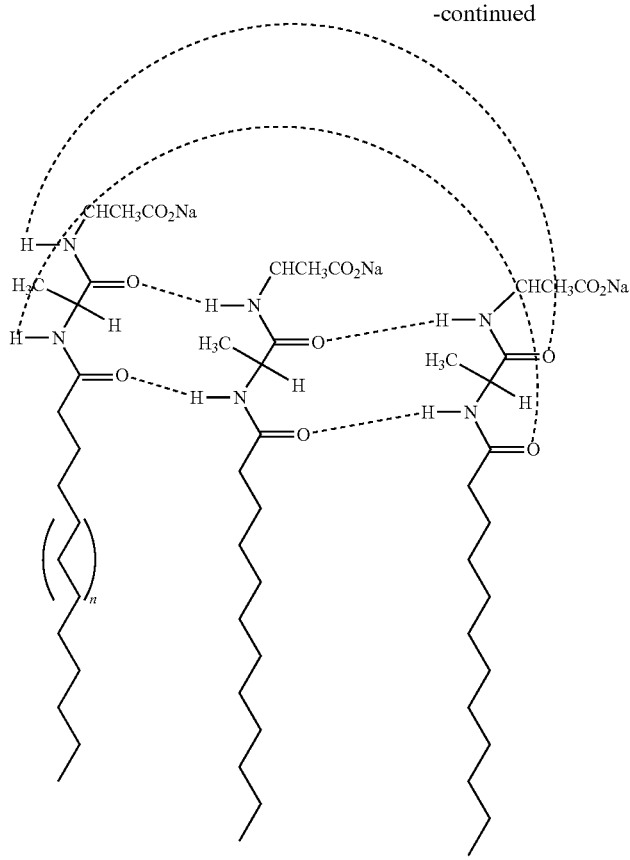

wherein n is 8-20,000; wherein n sodium N-lauroyl-L-alanyl-L-alanine molecules are linked in sequence by hydrogen bonds in the same plane, or n sodium N-lauroyl-L-alanyl-L-alanine molecules are linked in sequence by hydrogen bonds and the first and last molecules are also linked by hydrogen bonds to form a columnar structure.

The polymer sodium salt shown by Formula II' has a weight average molecular weight of between 5,000 and 5,000,000.

Method for Preparing Polymer or Salt Thereof

According to the present disclosure, there is provided a method for preparing a self-assembled amino acid supramolecular polymer, comprising the following steps:

Step I, dissolving L-alanine and a metallic inorganic base in a mixed solution of distilled water and an organic solvent, and stirring uniformly to obtain an L-alanine salt solution;

Step II, adding lauroyl chloride and a metallic inorganic base in sequence to the L-alanine salt solution obtained above to allow the reaction system to have a pH=8-10, and then continuing the stirring under certain conditions to obtain a pasty N-lauroyl-L-alanine salt;

Step III, acidifying the pasty N-lauroyl-L-alanine salt obtained above to a pH=3-4 to precipitate a white solid gradually, and then placing the resultant in an ice bath for 1-3 h, filtering to obtain a crude N-lauroyl-L-alanine product;

Step IV, adding a solvent, L-alanine and a catalyst to the crude N-lauroyl-L-alanine product obtained above, and stirring under certain conditions to obtain the self-assembled amino acid supramolecular polymer provided according to the present disclosure.

In one embodiment according to the present disclosure, a volume ratio of the distilled water to the organic solvent in Step I is 1: (1-1.5).

In one embodiment according to the present disclosure, a molar ratio of the L-alanine to the metallic inorganic base in Step I is 1: (1-1.5).

In one embodiment according to the present disclosure, the metallic inorganic base in Step I is selected from one or more of sodium hydroxide, potassium hydroxide, sodium carbonate, and potassium carbonate.

In one embodiment according to the present disclosure, the organic solvent in Step I is selected from one or more of acetone, methanol, ethanol, acetonitrile, and tetrahydrofuran.

In one embodiment according to the present disclosure, a feeding molar ratio of the lauroyl chloride to the L-alanine in Step II is (0.8-1):1.

In one embodiment according to the present disclosure, the stirring conditions in Step II include: temperature 5-50° C., time 0.5-3.5 hours.

In one embodiment according to the present disclosure, the metallic inorganic base in Step II has a concentration of 30-80%; the metallic inorganic base is selected from one or more of sodium hydroxide, potassium hydroxide, sodium carbonate, and potassium carbonate.

In one embodiment according to the present disclosure, the solvent in Step IV is selected from acetone, methanol, ethanol, acetonitrile, tetrahydrofuran, or mixed solvents made from one or more of the above solvents with water.

In one embodiment according to the present disclosure, the catalyst in Step IV is selected from one or more of sulfuric acid, p-toluenesulfonic acid, and emulsifiers.

In one embodiment according to the present disclosure, a molar ratio of the crude N-lauroyl-L-alanine product, the solvent, L-alanine, and the catalyst in Step IV is 1:(5-10):(0.2-1.1):(0.001-0.2); preferably 1:(5-10):(0.2-0.5):(0.01-0.2).

In one embodiment according to the present disclosure, the stirring conditions in Step IV include: temperature 25-100° C., pressure 5 kg-50 kg, time 1-3 hours.

In one embodiment according to the present disclosure, in Step IV, the stirring is followed by cooling and filtering to obtain a solid which is washed and then dried to obtain a self-assembled N-lauroyl-L-alanine polymer substantially free of lauric acid.

Use of Polymer or Salt Thereof

The self-assembled amino acid supramolecular polymer provided according to the present disclosure may be used to immobilize oily substances, and its salt may be used as a surfactant.

The self-assembled amino acid supramolecular polymer or its salt provided according to the present disclosure may be used widely in the fields of daily chemicals, agriculture, or pharmaceutical industry, for example, without limitation, for preparing toothpaste, skin care composition, laundry liquid, perfumed soap, laundry powder, cleanser essence, facial mask, etc.

The present disclosure will be further described below with reference to the accompanying drawings and examples. It is to be understood that these examples are only used to illustrate the present disclosure, not to limit the scope of the present disclosure. It is to be further understood that various changes or modifications to the present disclosure can be made by those skilled in the art after reading the above teachings of the present disclosure, and these equivalent variations fall in the scope defined by the accompanying claims of the application as well.

EXAMPLE 1 SYNTHESIS OF SELF-ASSEMBLED N-LAUROYL-L-ALANINE POLYMER

Embodiment 1

89 g (1 mol) L-alanine and 40 g (1 mol) sodium hydroxide were dissolved in a mixed solution of 150 mL distilled water and 150 mL acetone in a 1 L three-necked flask at ambient temperature, and stirred uniformly to obtain a sodium L-alanine solution.

Under the condition of 25° C., 218.7 g (1 mol) lauroyl chloride was added dropwise slowly to the L-alanine salt solution, and then a 50% sodium hydroxide solution was added dropwise to allow the reaction system to have a pH=9. After the addition was complete, stirring was continued for 2 h at 25° C. to obtain a pasty N-lauroyl-L-alanine salt.

Hydrochloric acid was added to the pasty N-lauroyl-L-alanine salt to acidify it to a pH=3-4. A white solid precipitated gradually. Then, the resultant was placed in an ice bath for 2 h. Filtering was conducted to obtain a crude N-lauroyl-L-alanine product.

A mixed solvent of water and acetone, L-alanine and p-toluenesulfonic acid were added to the crude N-lauroyl-L-alanine product, wherein the crude N-lauroyl-L-alanine product, the mixed solvent of water and acetone, L-alanine, and p-toluenesulfonic acid were added at a molar ratio of 1:7.5:0.35:0.002. Stirring was conducted for 2 h at a temperature of 60° C. and a pressure of 27 kg, so that lauric acid in a small amount was completely consumed. Then, cooling and filtering were conducted. The resulting solid was washed twice with pure water, and finally dried at 60° C. to obtain a self-assembled N-lauroyl-L-alanine polymer.

The mass of the resulting self-assembled N-lauroyl-L-alanine polymer was 250.5 g; the yield was 92.3%; the purity was higher than 97%; the content of lauric acid was not detectable; and the melting point was 82-84° C.

It was found by experimentation that, if stirring was conducted at ambient pressure for the above reaction, we still found a small amount of lauric acid by examining the reaction system. No self-assembled N-lauroyl-L-alanine polymer could be obtained in the final product.

Embodiment 2

89 g (1 mol) L-alanine and 56 g (1 mol) potassium hydroxide were dissolved in a mixed solution of 150 mL distilled water and 150 mL acetone in a 1 L three-necked flask at ambient temperature, and stirred uniformly to obtain a sodium L-alanine solution.

Under the condition of 25° C., 218.7 g (1 mol) lauroyl chloride was added dropwise slowly to the L-alanine salt solution, and then a 50% sodium hydroxide solution was added dropwise to allow the reaction system to have a pH=9. After the addition was complete, stirring was continued for 2 h at 25° C. to obtain a pasty N-lauroyl-L-alanine salt.

Hydrochloric acid was added to the pasty N-lauroyl-L-alanine salt to acidify it to a pH=3-4. A white solid precipitated gradually. Then, the resultant was placed in an ice bath for 2 h. Filtering was conducted to obtain a crude N-lauroyl-L-alanine product.

A mixed solvent of water and acetone, L-alanine and p-toluenesulfonic acid were added to the crude N-lauroyl-L-alanine product, wherein the crude N-lauroyl-L-alanine product, the mixed solvent of water and acetone, L-alanine, and p-toluenesulfonic acid were added at a molar ratio of 1:10:0.3:0.003. Stirring was conducted for 2 h at a temperature of 25° C. and a pressure of 43 kg, so that lauric acid in a small amount was completely consumed. Then, cooling and filtering were conducted. The resulting solid was washed twice with pure water, and finally dried at 60° C. to obtain a self-assembled N-lauroyl-L-alanine polymer.

The mass of the resulting self-assembled N-lauroyl-L-alanine polymer was 243.7 g; the yield was 89.8%; the purity was higher than 97%; the content of lauric acid was not detectable; and the melting point was 82-84° C.

Embodiment 3

89 kg (1 Kmol) L-alanine and 40 kg (1 Kmol) sodium hydroxide were dissolved in a mixed solution of 150 L distilled water and 150 L acetone in a 1000 L reaction kettle at ambient temperature, and stirred uniformly to obtain a sodium L-alanine solution.

Under the condition of 25° C., 175 kg (0.8 Kmol) lauroyl chloride was added dropwise slowly to the L-alanine salt solution, and then a 50% sodium hydroxide solution was added dropwise to allow the reaction system to have a pH=9. After the addition was complete, stirring was continued for 2 h at 25° C. to obtain a pasty N-lauroyl-L-alanine salt.

Hydrochloric acid was added to the pasty N-lauroyl-L-alanine salt to acidify it to a pH=3-4. A white solid precipitated gradually. Then, the resultant was placed in an ice bath for 2 h. Filtering was conducted to obtain a crude N-lauroyl-L-alanine product.

A mixed solvent of water and acetone, L-alanine and p-toluenesulfonic acid were added to the crude N-lauroyl-L-alanine product, wherein the crude N-lauroyl-L-alanine product, the mixed solvent of water and acetone, L-alanine, and p-toluenesulfonic acid were added at a molar ratio of 1:5:0.2:0.002. Stirring was conducted for 2 h at a temperature of 100° C. and a pressure of 50 kg, so that lauric acid in a small amount was completely consumed. Then, cooling and filtering were conducted. The resulting solid was washed twice with pure water, and finally dried at 60° C. to obtain a self-assembled N-lauroyl-L-alanine polymer.

The mass of the resulting self-assembled N-lauroyl-L-alanine polymer was 217.2 kg; the yield was 98.5%; the purity was higher than 97%; the content of lauric acid was not detectable; and the melting point was 82-84° C.

Embodiment 4

89 g (1 mol) L-alanine and 106 g (1 mol) sodium carbonate were dissolved in a mixed solution of 150 mL distilled water and 150 mL acetone in a 1 L three-necked flask at ambient temperature, and stirred uniformly to obtain a sodium L-alanine solution.

Under the condition of 50° C., 218.7 g (1 mol) lauroyl chloride was added dropwise slowly to the L-alanine salt solution, and then a 30% sodium hydroxide solution was added dropwise to allow the reaction system to have a pH=8. After the addition was complete, stirring was continued for 3.5 h at 25° C. to obtain a pasty N-lauroyl-L-alanine salt.

Hydrochloric acid was added to the pasty N-lauroyl-L-alanine salt to acidify it to a pH=3-4. A white solid precipitated gradually. Then, the resultant was placed in an ice bath for 3 h. Filtering was conducted to obtain a crude N-lauroyl-L-alanine product.

A methanol solution, L-alanine and sulfuric acid were added to the crude N-lauroyl-L-alanine product, wherein the crude N-lauroyl-L-alanine product, the methanol solution, L-alanine, and sulfuric acid were added at a molar ratio of 1:5:0.2:0.005. Stirring was conducted for 1 h at a temperature of 25° C. and a pressure of 5 kg, so that lauric acid in a small amount was completely consumed. Then, cooling and filtering were conducted. The resulting solid was washed twice with pure water, and finally dried at 70° C. to obtain a self-assembled N-lauroyl-L-alanine polymer.

The mass of the resulting self-assembled N-lauroyl-L-alanine polymer was 244.7 g; the yield was 90.2%; the purity was higher than 97%; the content of lauric acid was not detectable; and the melting point was 82-84° C.

Embodiment 5

89 g (1 mol) L-alanine and 106 g (1 mol) sodium carbonate were dissolved in a mixed solution of 150 mL distilled water and 150 mL acetone in a 1 L three-necked flask at ambient temperature, and stirred uniformly to obtain a sodium L-alanine solution.

Under the condition of 5° C., 218.7 g (1 mol) lauroyl chloride was added dropwise slowly to the L-alanine salt solution, and then a 80% sodium hydroxide solution was added dropwise to allow the reaction system to have a pH=10. After the addition was complete, stirring was continued for 0.5 h at 50° C. to obtain a pasty N-lauroyl-L-alanine salt.

Hydrochloric acid was added to the pasty N-lauroyl-L-alanine salt to acidify it to a pH=3-4. A white solid precipitated gradually. Then, the resultant was placed in an ice bath for 1 h. Filtering was conducted to obtain a crude N-lauroyl-L-alanine product.

A methanol solution, L-alanine and p-toluenesulfonic acid were added to the crude N-lauroyl-L-alanine product, wherein the crude N-lauroyl-L-alanine product, the methanol solution, L-alanine, and p-toluenesulfonic acid were added at a molar ratio of 1:5:0.2:0.002. Stirring was conducted for 3 h at a temperature of 100° C. and a pressure of 50 kg, so that lauric acid in a small amount was completely consumed. Then, cooling and filtering were conducted. The resulting solid was washed twice with pure water, and finally dried at 40° C. to obtain a self-assembled N-lauroyl-L-alanine polymer.

The mass of the resulting self-assembled N-lauroyl-L-alanine polymer was 235.4 g; the yield was 86.7%; the purity was higher than 97%; the content of lauric acid was not detectable; and the melting point was 82-84° C.

Embodiment 6

89 kg (1 Kmol) L-alanine and 40 kg (1 Kmol) sodium hydroxide were dissolved in a mixed solution of 150 L distilled water and 150 L acetone in a 1000 L reaction kettle at ambient temperature, and stirred uniformly to obtain a sodium L-alanine solution.

Under the condition of 25° C., 175 kg (0.8 Kmol) lauroyl chloride was added dropwise slowly to the L-alanine salt solution, and then a 50% sodium hydroxide solution was added dropwise to allow the reaction system to have a pH=9. After the addition was complete, stirring was continued for 2 h at 25° C. to obtain a pasty N-lauroyl-L-alanine salt.

Hydrochloric acid was added to the pasty N-lauroyl-L-alanine salt to acidify it to a pH=3-4. A white solid precipitated gradually. Then, the resultant was placed in an ice bath for 2 h. Filtering was conducted to obtain a crude N-lauroyl-L-alanine product.

A tetrahydrofuran solution, L-alanine and p-toluenesulfonic acid were added to the crude N-lauroyl-L-alanine product, wherein the crude N-lauroyl-L-alanine product, the tetrahydrofuran solution, L-alanine, and p-toluenesulfonic acid were added at a molar ratio of 1:7.5:0.2:0.002. Stirring was conducted for 2 h at a temperature of 63° C. and a pressure of 22.5 kg, so that lauric acid in a small amount was completely consumed. Then, cooling and filtering were conducted. The resulting solid was washed twice with pure water, and finally dried at 60° C. to obtain a self-assembled N-lauroyl-L-alanine polymer.

The mass of the resulting self-assembled N-lauroyl-L-alanine polymer was 218.2 kg; the yield was 99.0%; the purity was higher than 97%; the content of lauric acid was not detectable; and the melting point was 82-84° C.

EXAMPLE 2 STRUCTURAL CHARACTERIZATION OF SELF-ASSEMBLED N-LAUROYL-L-ALANINE POLYMER

1. Infrared Spectrum Analysis (GBT 6040-2002)

Instrument: Fourier Transform Infrared Spectrometer (FTS-1000)

Spectral conditions: the sample to be tested (self-assembled N-lauroyl-L-alanine polymer) and potassium bromide (spectrally pure, CP, purchased from Sinopharm Chemical Reagent Group) were thoroughly mixed at a ratio of 1:100, ground, and tablettized; the range of wave number for scan was 4000 cm$^{-1}$-400 cm$^{-1}$; the resolution was 4 cm$^{-1}$; the number of scans was 16.

Figure 1:
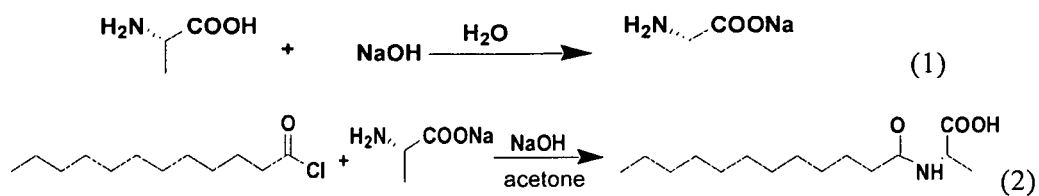
FIG. 1 shows the chemical reaction formulae for preparing N-lauroyl-L-alanine according to the synthetic method in Embodiment 3 in the present disclosure.
Figure 2:
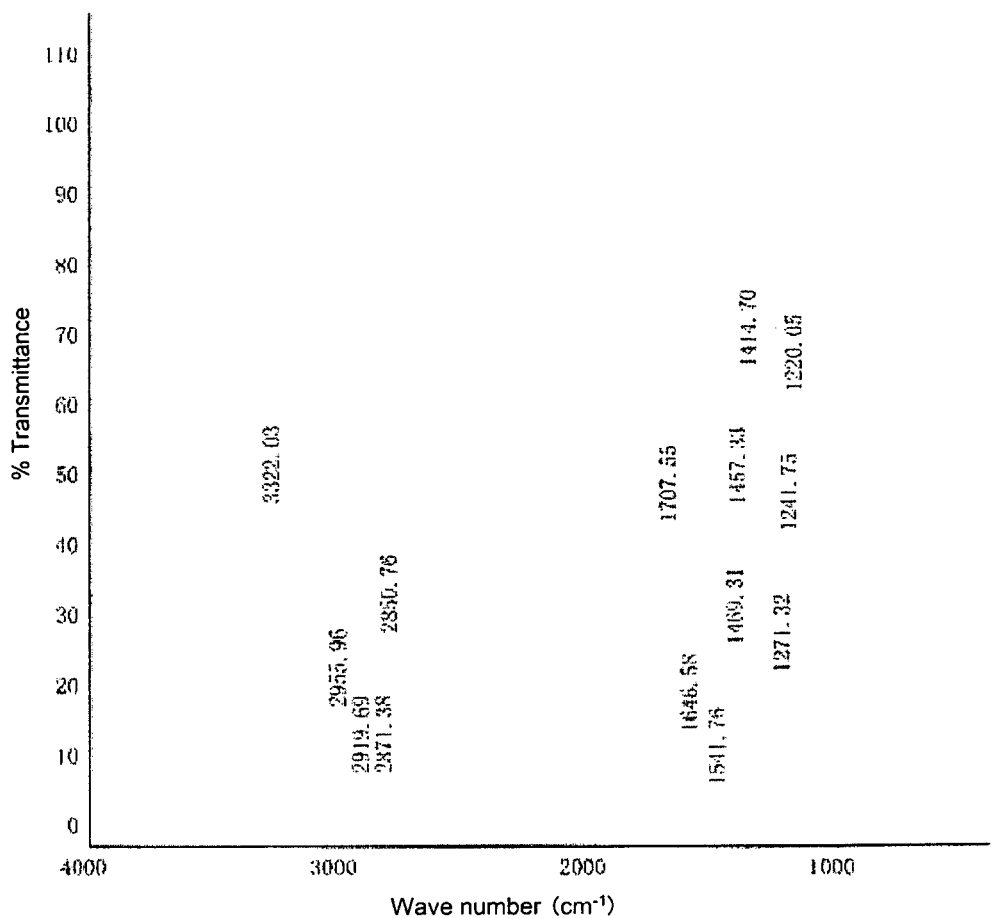
FIG. 2 shows an infrared spectrum diagram of the self-assembled N-lauroyl-L-alanine polymer obtained according to the synthetic method in Embodiment 3 in the present disclosure.

FIG. 2 shows an infrared spectrum diagram of the self-assembled N-lauroyl-L-alanine polymer synthesized according to the method in Embodiment 3 in the present disclosure. As shown by FIG. 2, the infrared spectral data of the self-assembled N-lauroyl-L-alanine polymer synthesized according to the method in Embodiment 3 in the present disclosure are as follows:

IR Vmax(KBr): 3322 cm-1 (N—H); 2955 cm-1, 2871 cm-1, 1377 cm-1 (CH3); 2919 cm-1, 2850 cm-1, 1469 cm-1, 720 cm-1 (=CH2); 1646 cm-1 (C=O); 1541 cm-1 (C—N, N—H); 1271 cm-1, 2120 cm-1 (COOH); 1707 cm-1 (C=O); 1414 cm-1 (—OH); 1241 cm-1 (C—O).

2. NMR Analysis (JY/T 007-1996)

Figure 3A:
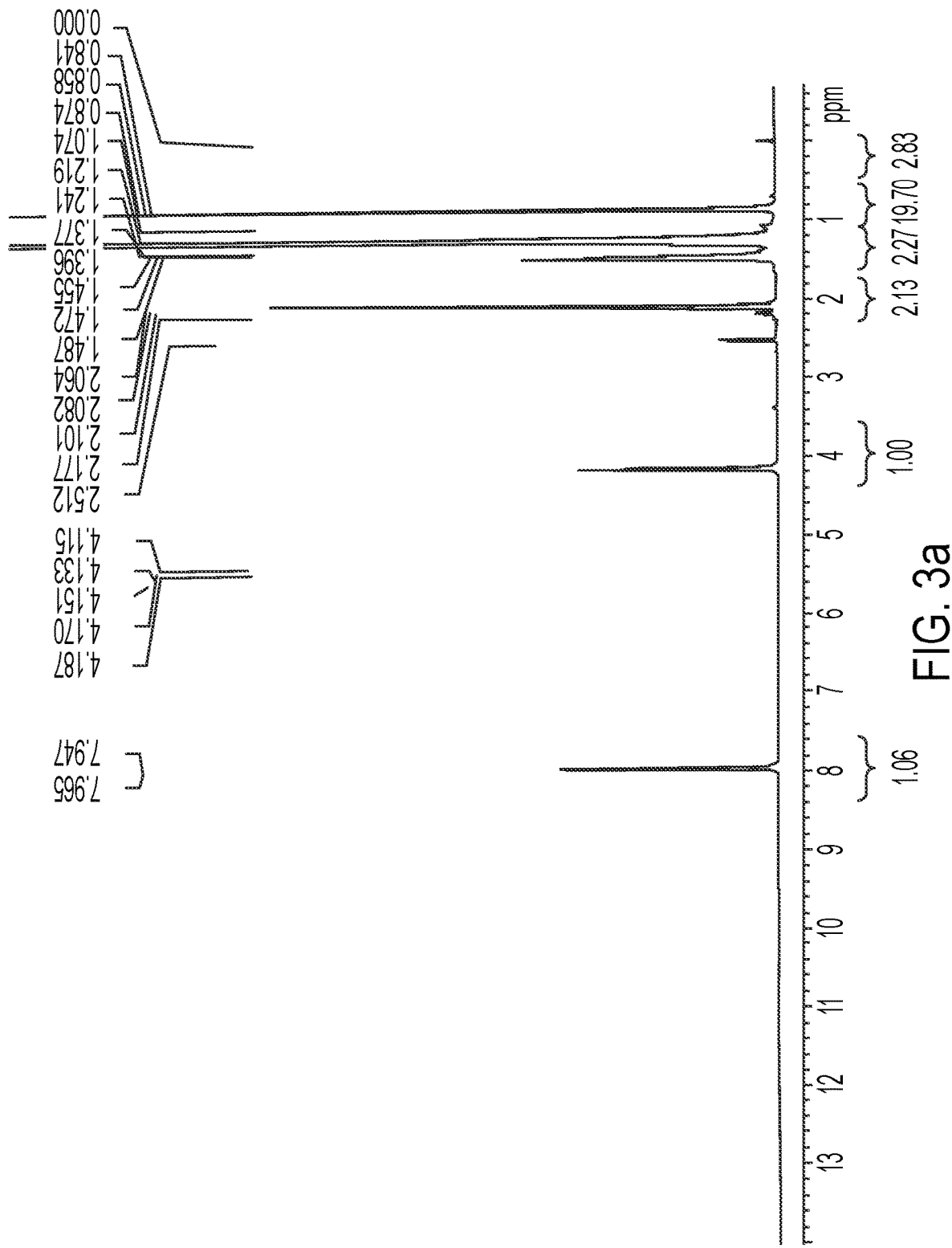
FIG. 3a shows a $^1$H-NMR spectrum of the self-assembled N-lauroyl-L-alanine polymer obtained according to the synthetic method in Embodiment 3 in the present disclosure.
Figure 3B:
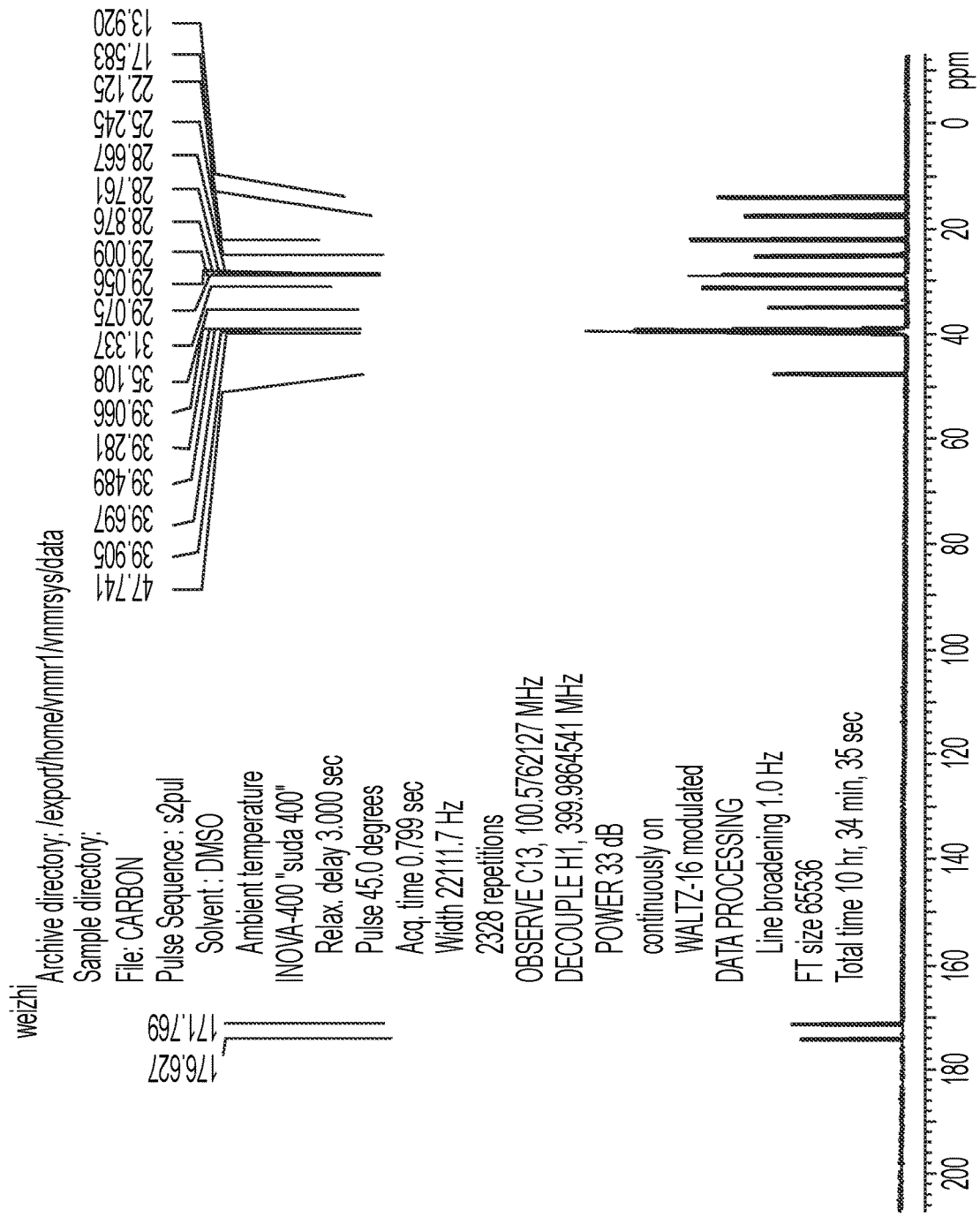
FIG. 3b shows a $^{13}$C-NMR spectrum of the self-assembled N-lauroyl-L-alanine polymer obtained according to the synthetic method in Embodiment 3 in the present disclosure.

The resulting self-assembled N-lauroyl-L-alanine polymer was subjected to NMR analysis using UNITY-400 NMR spectrometer. FIG. 3a shows the $^1$H-NMR spectrum of the self-assembled N-lauroyl-L-alanine polymer obtained according to the synthetic method in Embodiment 3 in the present disclosure; FIG. 3b shows the $^{13}$C-NMR spectrum of the self-assembled N-lauroyl-L-alanine polymer obtained according to the synthetic method in Embodiment 3 in the present disclosure. The data obtained by NMR are as follows:

$^1$H NMR(DMSO): δ7.95 (d, 1H); 4.15 (m, 1H); 2.08 (t, 2H); 1.48 (m, 2H); 1.2 (m, 19H); 0.86 (t, 3H);

$^{13}$C NMR(CDCl3): δ 174.63; 171.77; 47.74; 35.11; 31.33; 29.08; 29.06; 29.01; 28.87; 28.76; 28.67; 25.24; 22.13; 18.03; 13.92.

3. HPLC Analysis (GBT 16631-2008)

In the high performance liquid chromatography analysis, an ultraviolet detector was used to identify and determine the self-assembled N-lauroyl-L-alanine polymer. The retention time of the self-assembled N-lauroyl-L-alanine polymer sample was compared with that of a standard to identify the substance, and an area normalization method was used for quantification. Unless otherwise specified, all reagents were chromatographically pure, and water was ultrapure water.

Method for formulating a 20 mmol buffer salt solution (pH 3.0): 1.36 g potassium dihydrogen phosphate ($KH_2PO_4$) was weighed (accurate to 0.001 g), placed in a 100 mL beaker, dissolved by adding water, and then transferred to a 500 mL volumetric flask. Water was added to the constant volume mark, and a 20 mmol potassium dihydrogen phosphate solution was obtained. Its pH was adjusted to 3.0 with phosphoric acid to obtain a buffer salt solution.

Instrument: high performance liquid chromatograph: equipped with a UV detector; a chromatographic column: ODS-2 HYPERSIL C18 250*4.6 mm 5 μm; a mobile phase vacuum filtration and degassing device; and 0.45 μm organic filter membrane.

Measurement:

(1) Preparation of Standard Sample Solution

A 30 mg N-lauroyl-L-alanine standard sample was weighed accurately, dissolved in an appropriate amount of the mobile phase, transferred to a 10 mL volumetric flask, diluted to the constant volume mark, and shaken fully. The solution was filtered with a 0.45 μm organic filter membrane, and the filtrate was stored for use.

(2) Preparation of Test Sample Solution

A 150 mg self-assembled N-lauroyl-L-alanine polymer sample to be tested was weighed accurately, dissolved in an appropriate amount of the mobile phase, transferred to a 50 mL volumetric flask, diluted to the constant volume mark, and shaken fully. The solution was filtered with a 0.45 μm organic filter membrane, and the filtrate was stored for use.

(3) Chromatographic Conditions

Mobile phase: methanol: 20 mmol buffer salt solution (pH 3.0)=70:30 (v/v); flow rate: 1.0 mL/min; column temperature: 30° C.; detection wavelength: 210 nm; injection volume: 20 μL.

(4) Sample Measurement

The instrument parameters were adjusted according to the chromatographic conditions. After the baseline of the instrument was stable, 20 μL of the standard sample solution and 20 μL of the test sample solution were injected into the chromatographic column respectively, and the chromatograms of the N-lauroyl-L-alanine standard sample solution and the test sample solution were recorded. The chromatographic peak of N-lauroyl-L-alanine in the test sample was qualitatively determined according to the retention time of the standard solution. The percentage of the test substance was determined from the peak area of the test sample using the area normalization method.

Figure 4:
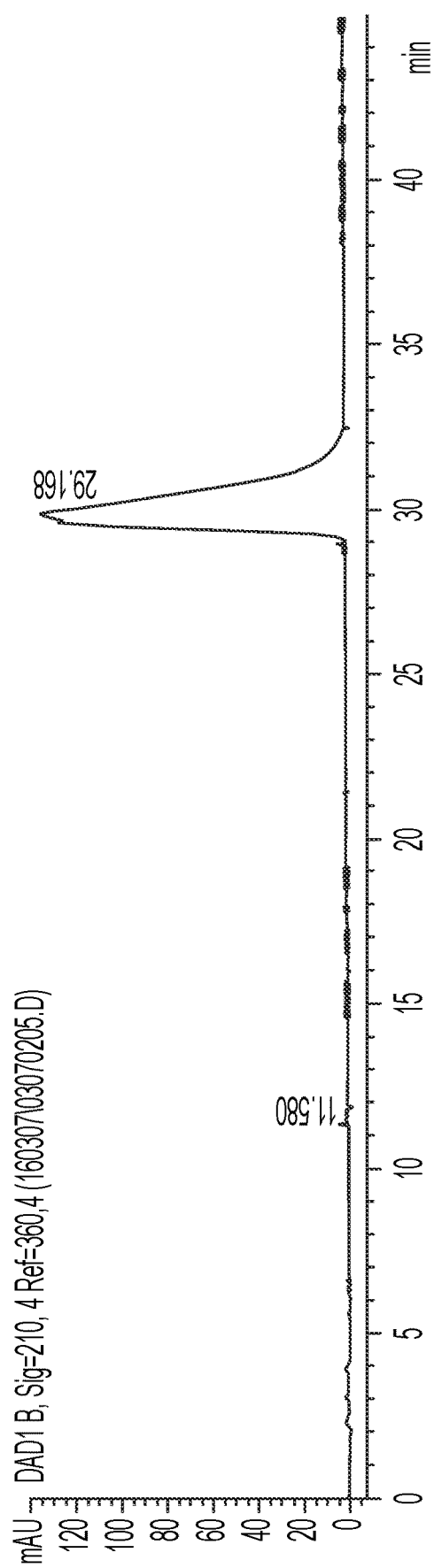
FIG. 4 shows a standard chromatogram of N-lauroyl-L-alanine.
Figure 5:
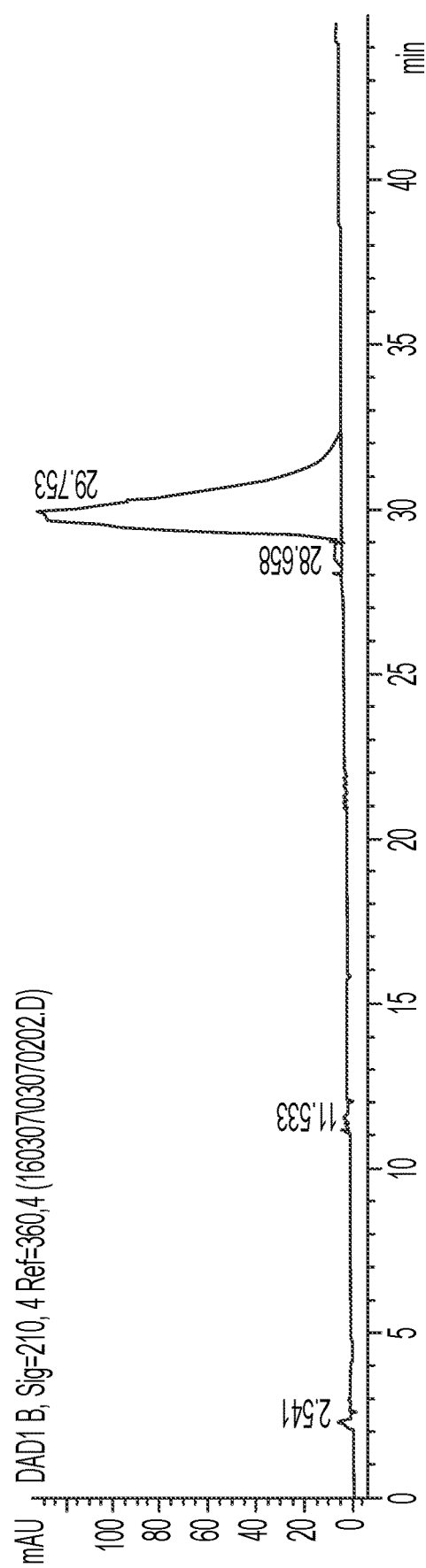
FIG. 5 shows a high performance liquid chromatogram of the self-assembled N-lauroyl-L-alanine polymer obtained according to the synthetic method in Embodiment 3 in the present disclosure, measured under the same conditions as those for obtaining FIG. 4.
Figure 6:
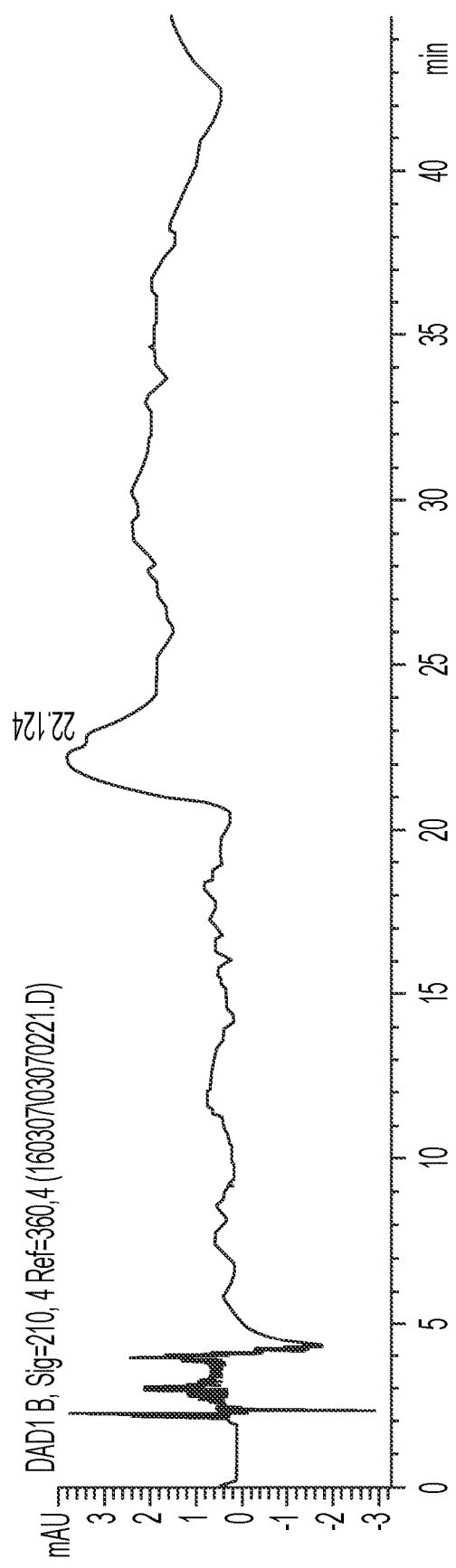
FIG. 6 shows a high performance liquid chromatogram of lauric acid measured under the same conditions as those for obtaining FIG. 4.
Figure 7:
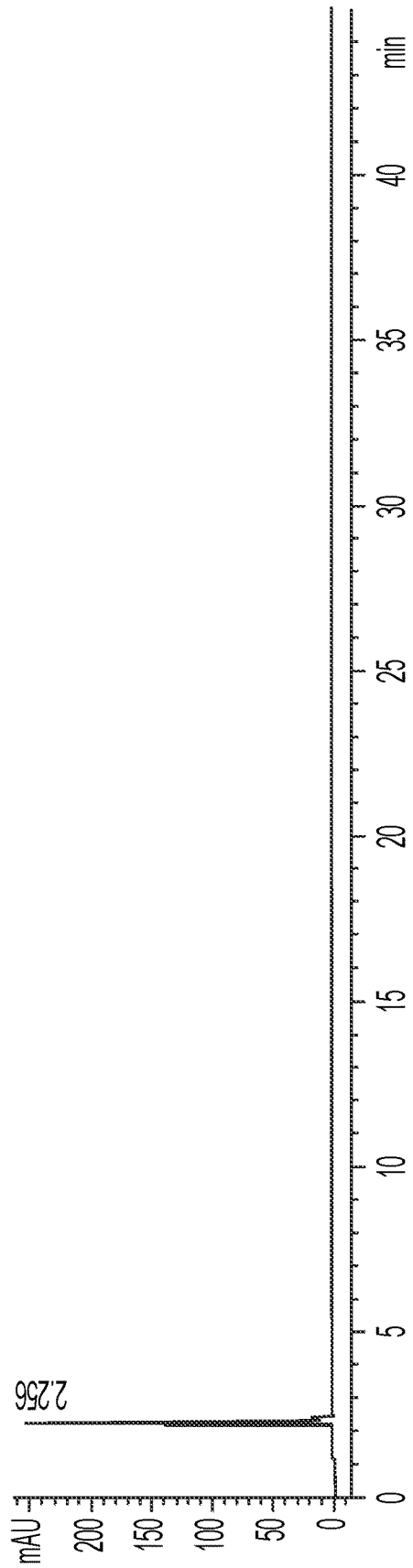
FIG. 7 shows a high performance liquid chromatogram of L-alanine measured under the same conditions as those for obtaining FIG. 4.
Figure 8:
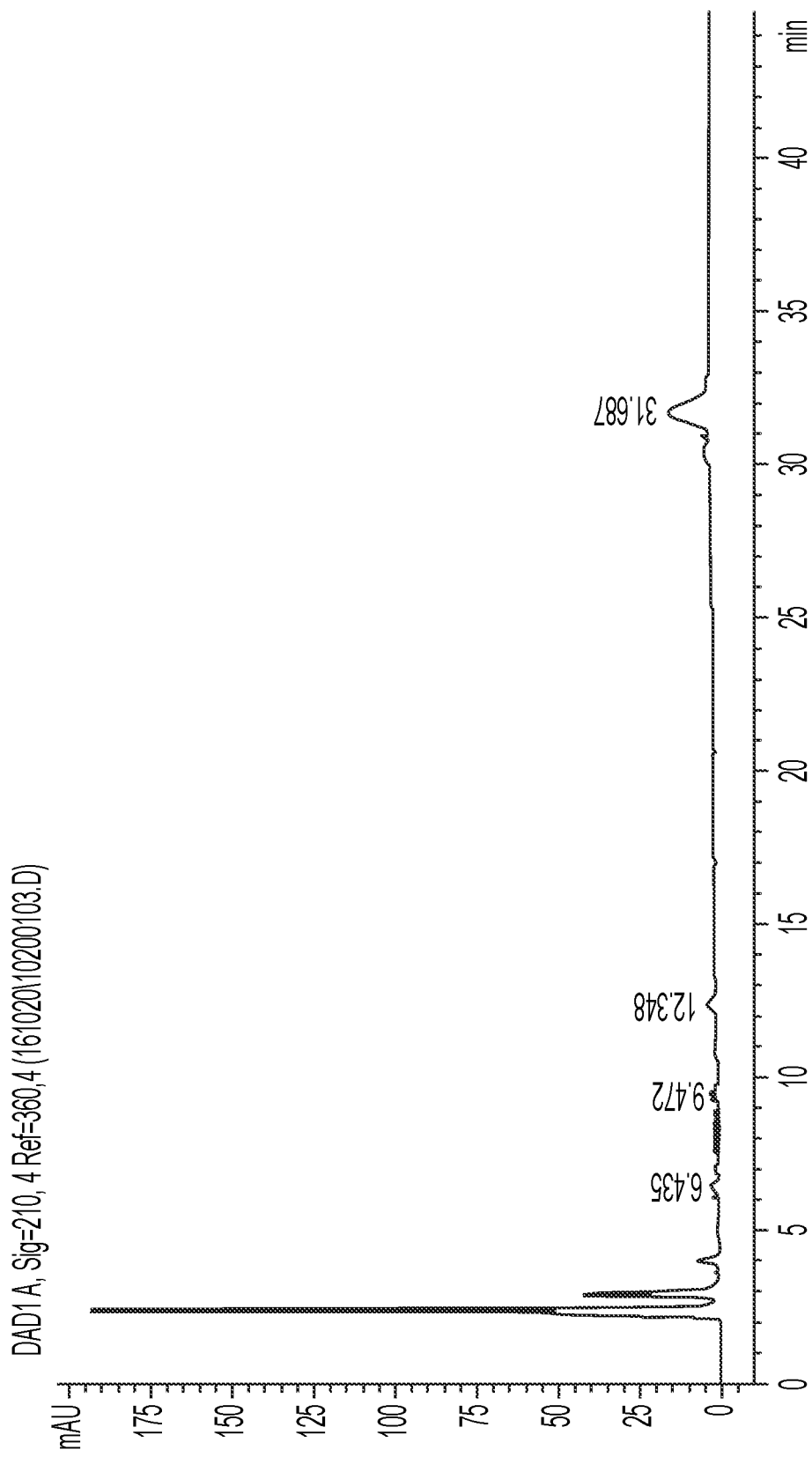
FIG. 8 shows a high performance liquid chromatogram of N-lauroyl-L-alanyl-L-alanine obtained by column preparation and separation, measured under the same conditions as those for obtaining FIG. 4.

FIG. 4 shows a standard chromatogram of N-lauroyl-L-alanine; FIG. 5 shows a high performance liquid chromatogram of the self-assembled N-lauroyl-L-alanine polymer obtained according to the synthetic method in Embodiment 3 in the present disclosure, measured under the same conditions as those for obtaining FIG. 4; FIG. 6 shows a high performance liquid chromatogram of lauric acid measured under the same conditions as those for obtaining FIG. 4; FIG. 7 shows a high performance liquid chromatogram of L-alanine measured under the same conditions as those for obtaining FIG. 4; FIG. 8 shows a high performance liquid chromatogram of N-lauroyl-L-alanyl-L-alanine obtained by column preparation and separation, measured under the same conditions as those for obtaining FIG. 4. As can be seen from FIGS. 4-8, the self-assembled N-lauroyl-L-alanine polymer prepared by the inventive synthetic method was free of lauric acid among the impurities, and its purity was 97% or higher. The major impurity was N-lauroyl-L-alanyl-L-alanine which was contemplated to be formed by further dehydration condensation of N-lauroyl-L-alanine and L-alanine during the reaction process.

4. Mass Spectrometry Analysis

The sample was injected into an Agilent 1200/6220 LC/MS instrument, and a mass spectrum (FIG. 20) of N-lauroyl-L-alanine was obtained by analysis. The molecular formula of N-lauroyl-L-alanine is $C_{15}H_{29}NO_3$, and the theoretical value of the characteristic peak of the mass spectrum [M+H]+ is 272.222. The measured value is 272.2223, having a deviation of 1.03 ppm from the theoretical value. [M+Na]+ is 294.204, while the measured value is 294.2034, having a deviation of 2.08 ppm from the theoretical value. The measured value of the sample is consistent with the mass spectrum characteristic peak of the substance with the molecular formula $C_{15}H_{29}NO_3$. No molecular ion peak of lauric acid was found in FIG. 20. Because of the extremely high sensitivity of mass spectrometry, it can be qualitatively judged from the mass spectrum that the N-lauroyl-L-alanine sample was free of lauric acid.

5. Optical Rotation Analysis

As measured using a polarimeter, the (specific) optical rotation of N-lauroyl-L-alanine was: $[\alpha]_{20° C.}^{D}$=−14.7° to −16.7° (C=2, $CH_3OH$).

6. Description of Structural Features

Figure 9:
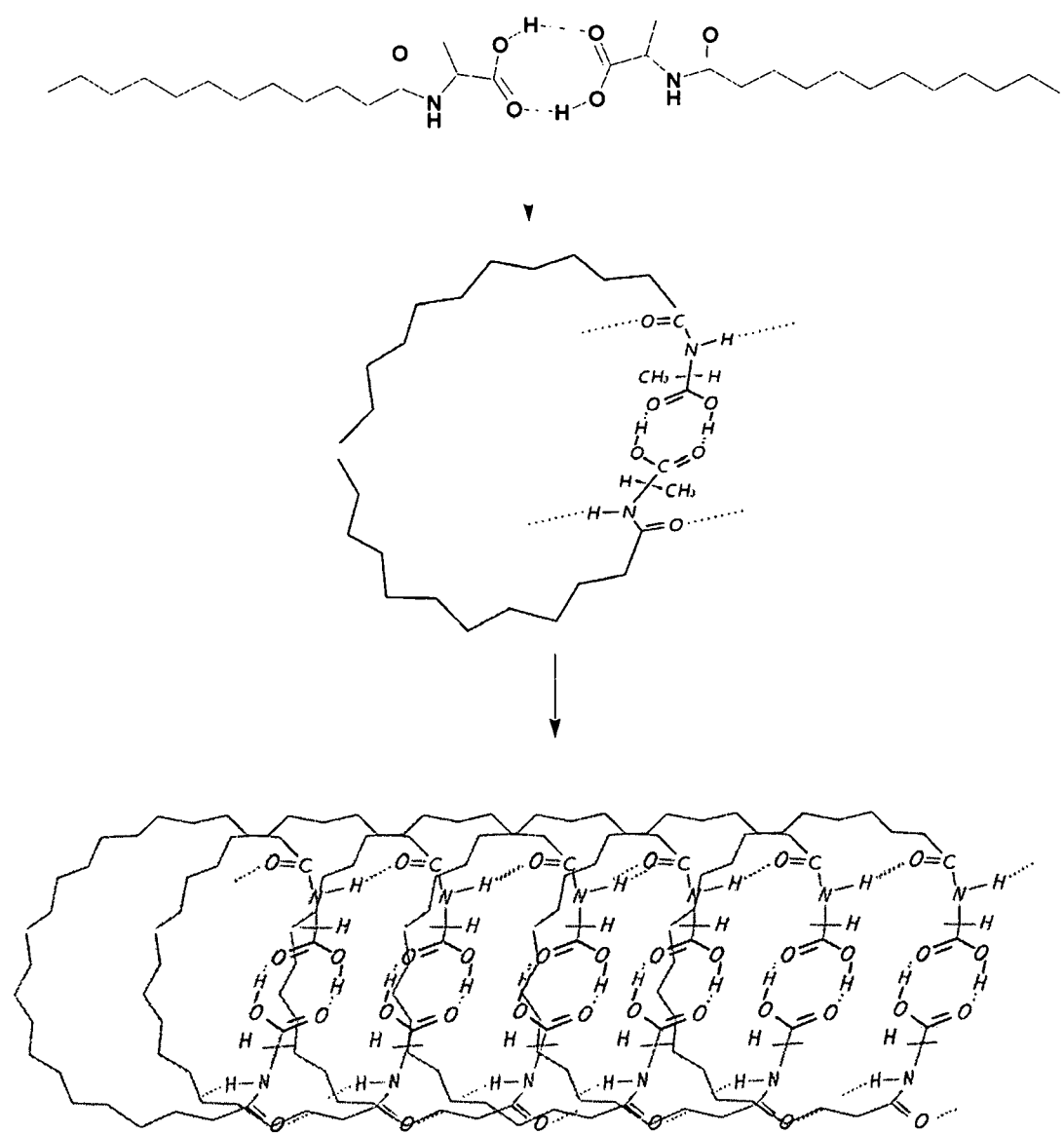
FIG. 9 is a diagram demonstrating formation of the structure of a supramolecular amino acid from the N-lauroyl-L-alanine monomer obtained according to the synthetic method in Embodiment 3 in the present disclosure.

FIG. 9 is a diagram demonstrating formation of the structure of a supramolecular amino acid from the N-lauroyl-L-alanine monomer obtained according to the synthetic method in Embodiment 3 in the present disclosure. As can be seen from the above infrared, NMR, HPLC analysis and optical rotation measurement, the self-assembled N-lauroyl-L-alanine polymer produced by the inventive process was free of lauric acid as an impurity. The N-lauroyl-L-alanine synthesized in the process can form two groups of hydrogen bonds, and N-lauroyl-L-alanyl-L-alanine can form three groups of hydrogen bonds. Two carboxyl groups of N-lauroyl-L-alanine are linked by hydrogen bonds, and there is an alkane structure of an eleven-carbon chain at each of both ends. According to the principle of oil-oil compatibility, the two lipophilic ends are coupled like a chain, connected end to end to form a ring. Also by means of hydrogen bonds and oil-oil compatibility, countless rings stack to form a columnar molecular cluster, and countless columnar molecular clusters further stack to form a special spatial structure—referred to as a self-assembled supramolecular amino acid polymer.

Figure 10A:
FIG. 10a shows a 300× electron micrograph of the self-assembled N-lauroyl-L-alanine polymer obtained according to the synthetic method in Embodiment 3 in the present disclosure.
Figure 10B:
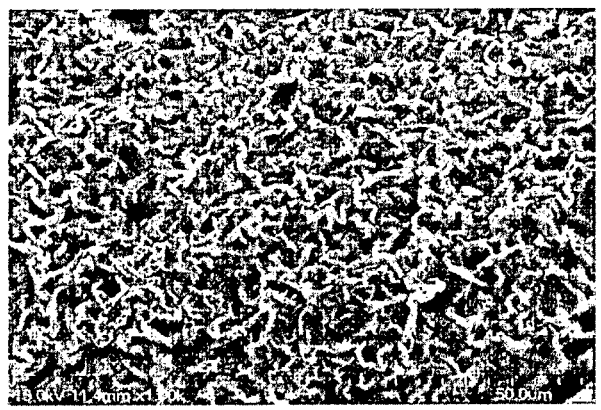
FIG. 10b shows a 1000× electron micrograph of the self-assembled N-lauroyl-L-alanine polymer obtained according to the synthetic method in Embodiment 3 in the present disclosure.
Figure 10C:
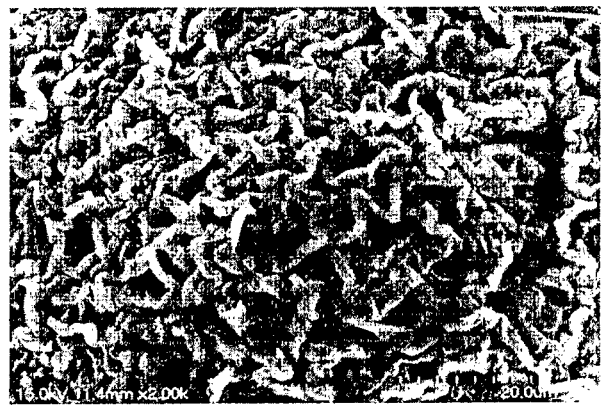
FIG. 10c shows a 2000× electron micrograph of the self-assembled N-lauroyl-L-alanine polymer obtained according to the synthetic method in Embodiment 3 in the present disclosure.

FIGS. 10a, 10b and 10c show the 300×, 1000× and 2000× electron micrographs of the self-assembled N-lauroyl-L-alanine polymer obtained according to the synthetic method in Embodiment 3 in the present disclosure respectively. As shown by FIGS. 10a, 10b and 10c, the inventive self-assembled N-lauroyl-L-alanine polymer has a microstructure like a hemp cord which is entangled to form a "supramolecular amino acid". FIGS. 9, 10a, 10b and 10c prove in a better way the principle by which the N-lauroyl-L-alanine monomer forms the supramolecular amino acid, and the structure thereof.

Figure 12:
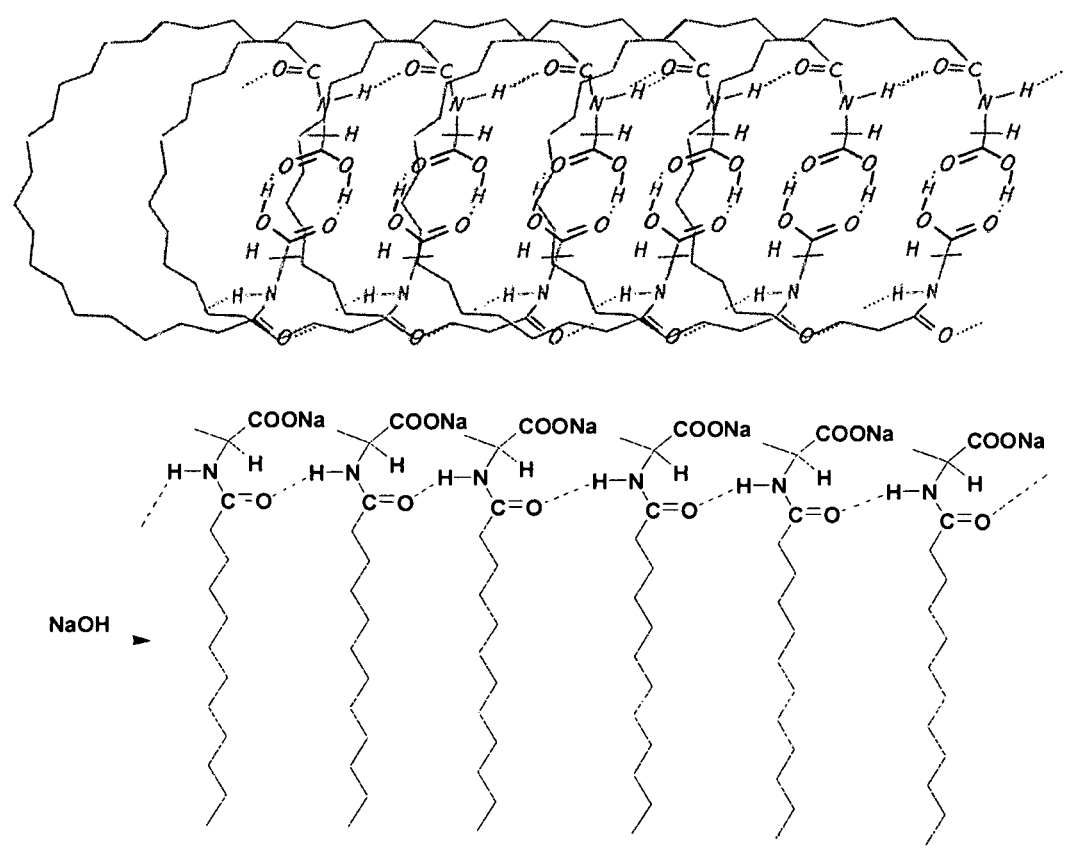
FIG. 12 is a diagram demonstrating further formation of a sodium salt from the supramolecular amino acid formed from the self-assembled N-lauroyl-L-alanine obtained according to the synthetic method in Embodiment 3 in the present disclosure.
Figure 13:
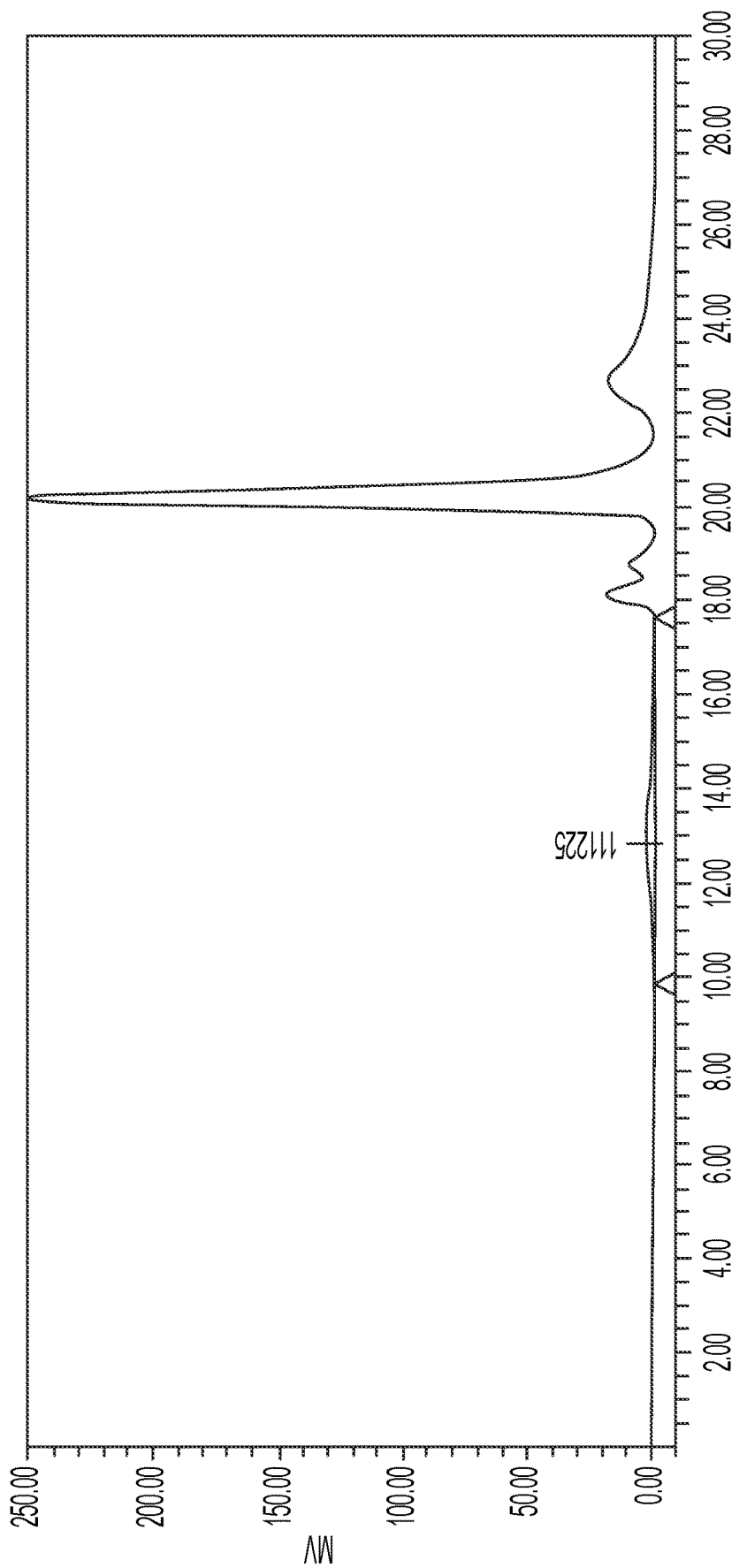
FIG. 13 shows a diagram and data about the molecular weight of the sodium salt of the supramolecular amino acid further formed from the self-assembled N-lauroyl-L-alanine obtained according to the synthetic method in Embodiment 3 in the present disclosure.

After the supramolecular amino acid was formed, the supramolecular amino acid further reacted with sodium hydroxide to form a sodium salt structure of the supramolecular amino acid, as shown by FIG. 12. Sodium N-lauroyl-L-alanine, as the basic unit, self-assembled into a supramolecular polymer through hydrogen bonding. The weight average molecular weight was measured to be 125841, as shown by FIG. 13. As shown by FIG. 12, the sodium salt structure is hydrophilic at one side and oleophilic at the other side. The molecules are linked by hydrogen bonds to form a special two-dimensional network structure having a regular arrangement. The sodium salt has a strong ability to combine with oil, and can be used as a primary surfactant.

Figure 11A:
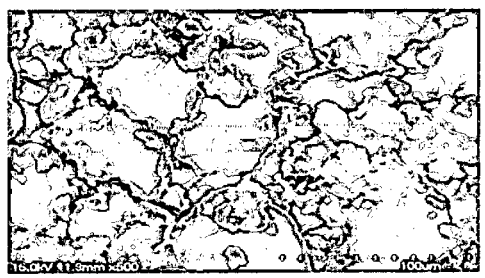
FIG. 11a shows a 500× electron micrograph of commercially available N-lauroyl-L-alanine (containing 2-5% lauric acid)
Figure 11B:
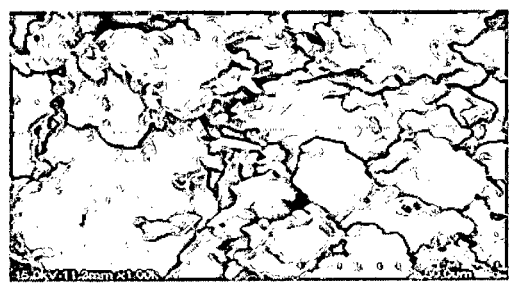
FIG. 11b shows a 1000× electron micrograph of commercially available N-lauroyl-L-alanine (containing 2-5% lauric acid)
Figure 11C:
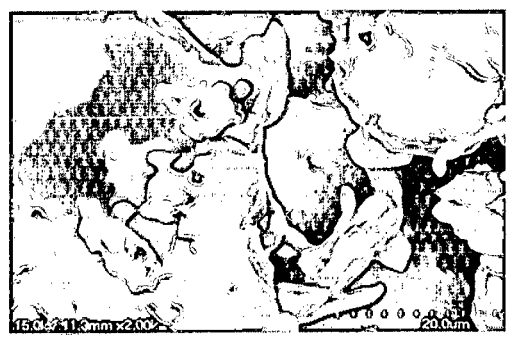
FIG. 11c shows a 2000× electron micrograph of commercially available N-lauroyl-L-alanine (containing 2-5% lauric acid)

In addition, commercially available N-lauroyl-L-alanine (purchased from Changsha Puji Biotechnology Co., Ltd.) was also measured with scanning electron microscopy herein, wherein the N-lauroyl-L-alanine contained 0.21%-5% lauric acid. The scan results are shown by FIGS. 11a, 11b, and 11c. FIGS. 11a, 11b, and 11c show the 500×, 1000×, and 2000× electron micrographs of the commercially available N-lauroyl-L-alanine containing 0.21%-5% lauric acid respectively. As shown by FIGS. 11a, 11b, and 11c, the commercially available N-lauroyl-L-alanine in these electron micrographs exhibits a state in which the structure is arranged irregularly. Different from the corresponding 300×, 1000×, and 2000× electron micrographs of the N-lauroyl-L-alanine obtained by the inventive process according to the present disclosure, there is no hemp-cord-like or columnar structure like that in the electron micrographs of the inventive N-lauroyl-L-alanine. The reason for this is that the commercially available N-lauroyl-L-alanine contains lauric acid. The presence of lauric acid prevents formation of infinite hydrogen bond linkages between N-lauroyl-L-alanine molecules, thereby changing the structure and properties of N-lauroyl-L-alanine.

The inventive process effectively solves the problem that the residual lauric acid impurity damages the N-lauroyl-L-alanine structure, and further affects or damages the properties of N-lauroyl-L-alanine. As a result, hydrogen bonds can form easily between N-lauroyl-L-alanine molecules which are thus linked infinitely, and special properties are provided. The N-lauroyl-L-alanyl-L-alanine impurity generated in this process can also form hydrogen bonds, just like N-lauroyl-L-alanine. As such, the structural stability of this impurity is consolidated, and at the same time, the properties of N-lauroyl-L-alanine are not affected.

In further experiments herein, N-decanoyl-L-alanine was used to conduct structural studies under the same conditions, but the aforementioned three-dimensional network structure was not found. The reason may be that the carbon chain of N-decanoyl-L-alanine is short, and the lipophilic ends of two molecules cannot form a ring. It can thus be inferred that the carbon chain of the lipophilic group should have 12-18 carbons, and the fatty acyl-L-alanine formed from such a carbon chain with L-alanine can also form the aforementioned spatial structure by way of intermolecular hydrogen bonding and oil-oil compatibility with fatty acid being removed. Once this structure is formed, it is very stable. Experiments prove that the addition of less than 10% fatty acid will not damage the stability and properties of the existing structure, and thus will not affect its applications.

EXAMPLE 3 APPLICATIONS OF SELF-ASSEMBLED N-LAUROYL-L-ALANINE POLYMER

Application Embodiment 1 Evaluation of Inhibitory Effect of Self-Assembled N-Lauroyl-L-Alanine Polymer on Bacteria 10 g of the self-assembled N-lauroyl-L-alanine polymer synthesized according to the method in Embodiment 3 was added to water, and neutralized to pH=6-7 by adding a 10% aqueous sodium hydroxide solution, thereby formulating a 100 mL aqueous solution. 5 mL of the stock solution was used separately to soak fruit plates pre-inoculated with common bacteria such as *Staphylococcus aureus, Escherichia coli, Pseudomonas aeruginosa, Candida albicans*, etc, respectively. After a certain period of time of action, the plates were rinsed once with clean water, and then residual bacteria on the fruit plates were determined. The test results are shown in Table 1:

TABLE 1

| | Analysis on the antibacterial effect of the self-assembled N-lauroyl-L-alanine polymer | | | | |
|---|---|---|---|---|---|
| No. | Test items | Unit | Technical requirement | Test result | Individual evaluation |
| 1 | Bacteriostasis rate for *Escherichia coli* (8099), % (action for 2 minutes) | — | — | 96.3 | — |
| 2 | Bacteriostasis rate for *Escherichia coli* (8099), % (action for 5 minutes) | — | — | 100 | — |

TABLE 1-continued

Analysis on the antibacterial effect of the
self-assembled N-lauroyl-L-alanine polymer

| No. | Test items | Unit | Technical requirement | Test result | Individual evaluation |
|---|---|---|---|---|---|
| 3 | Bacteriostasis rate for *Staphylococcus aureus* (ATCC 6538), % (action for 2 minutes) | — | — | 100 | — |
| 4 | Bacteriostasis rate for *Staphylococcus aureus* (ATCC 6538), % (action for 5 minutes) | — | — | 100 | — |
| 5 | Bacteriostasis rate for *Candida albicans* (ATCC 10231), % (action for 5 minutes) | — | — | 100 | — |
| 6 | Total number of bacteria | CFU/mL | ≤1000 | <10 | Qualified |
| 7 | Number of coliforms | MPN/100 mL | ≤3 | <3 | Qualified |

As can be seen from the above data, the self-assembled N-lauroyl-L-alanine polymer solution synthesized according to the inventive method had a significant inhibitory effect on *Escherichia coli, Staphylococcus aureus* and *Candida albicans*. After the stock solution, i.e. the self-assembled N-lauroyl-L-alanine polymer solution, was applied to *Escherichia coli* for 2 minutes, the bacteriostasis rate reached 96.3%, and the bacteriostasis rate came to 100% after 5 minutes. After the stock solution was applied to *Staphylococcus aureus* for 2 minutes, the bacteriostasis rate reached 100%. The bacteriostasis rate also reached 100% when the stock solution acted on *Candida albicans* for 5 minutes.

As known from the common knowledge in the art, the size of bacteria is usually 0.5-5 μm. The gap between the columnar clusters of the supramolecular structure formed from the inventive N-lauroyl-L-alanine free of lauric acid is also micron sized, so bacteria can be entrapped and removed. Hence, it can be said that nano-sized foam micropores can be produced.

Application Embodiment 2 Evaluation of Pesticide Removing Effect of Self-Assembled N-Lauroyl-L-Alanine Polymer 100 g of a green vegetable (*Brassica chinensis* L.) in two portions were sprayed with pesticides (methamidophos and acephate) in advance. One portion was directly soaked in 1 L clean water, and then taken out for detection of residual pesticide on the vegetable leaves. The result is designated as "pre-rinse". The other portion was rinsed with a solution formulated using the self-assembled N-lauroyl-L-alanine polymer synthesized according to the method in Embodiment 3. The measurement result is designated as "post-rinse". The operation is described as follows:

10 g of the self-assembled N-lauroyl-L-alanine polymer synthesized according to the method in Embodiment 3 was added to water, and neutralized to pH=6-7 by adding a 10% aqueous sodium hydroxide solution, thereby formulating a 100 mL aqueous solution. The other portion of the 100 g green vegetable (*Brassica chinensis* L.) sprayed with the pesticides (methamidophos and acephate) in advance was cut into small pieces, soaked in 5 mL of the stock solution for 2 minutes, taken out, flushed with 500 mL clean water, and then taken out for detecting residual pesticide on the vegetable leaves. Table 2 shows data comparing residual pesticides before and after the rinsing:

TABLE 2

Analysis on pesticide removing effect of self-assembled N-lauroyl-L-alanine polymer

| No. | Test item | Pre-rinsing mg/kg | Post-rinsing mg/kg | Removal rate % |
|---|---|---|---|---|
| 1 | methamidophos | 16.06 | 5.68 | 64.63 |
| 2 | acephate | 38.48 | 9.75 | 74.66 |

As can be seen from the above data, the self-assembled N-lauroyl-L-alanine polymer solution, a surface active substance used in the present disclosure, has a significant effect in removing methamidophos and acephate. After the action for 2 minutes, the removal rate of methamidophos reached 64.63%; and the removal rate of acephate reached 74.66%. The effect is obvious.

Application Embodiment 3 Evaluation of Deodoring Effect of Self-Assembled N-Lauroyl-L-Alanine Polymer 10 g of the self-assembled N-lauroyl-L-alanine polymer synthesized according to the method in Embodiment 3 was added to water, and neutralized to pH=6-7 by adding a 10% aqueous sodium hydroxide solution, thereby formulating a 100 mL aqueous solution. 10 square centimeters of cotton cloth with peculiar smell (odor, engine oil smell, bad odor, etc.) was soaked in 5 mL of the stock solution for 2 minutes, taken it out, washed with water, and dried. The experiment results showed that all the peculiar smell on the cotton cloth disappeared. It can be seen that the self-assembled N-lauroyl-L-alanine polymer synthesized according to the inventive method has a good deodoring effect.

As can be seen from the above description, the inventive preparation method of the self-assembled N-lauroyl-L-alanine polymer has simple process steps and mild reaction conditions, and is thus suitable for industrial production. The self-assembled N-lauroyl-L-alanine polymer prepared by the inventive method has a high purity which is substantially 97% or higher, and the lauric acid content is between 0.0001% and 0.02%. Hence, the influence of lauric acid on product quality is effectively avoided. The resulting self-assembled N-lauroyl-L-alanine polymer is stable in structure and properties. It has sound bacteriostasis rates, wherein the bacteriostasis rates for *Escherichia coli*, *Staphylococcus aureus* and *Candida albicans* can all reach 100%. It can remove residual pesticide effectively, wherein the removal rate of methamidophos can reach 64.63%, and the removal rate of acephate can reach 74.66%. At the same time, it has a good deodoring ability. It is promising for use in the daily chemical industry, agriculture, and pharmaceutical industry.

Application Embodiment 4 Use of Self-Assembled N-Lauroyl-L-Alanine Polymer for Skin Care

TABLE 3

Starting materials and weight percentages thereof for skin care compositions

| Starting materials | Formula 1 | Formula 2 | Formula 3 | Formula 4 | Formula 5 | Formula 6 | Formula 7 |
|---|---|---|---|---|---|---|---|
| Natural oil mixture* | 57 | 80 | 64.3 | 64 | 65 | 51 | 57 |
| Corn starch | 40 | 15 | 25 | 25 | 0 | 25 | 40 |
| KTZ classical white mica | 0 | 0 | 0.5 | 0 | 0 | 0 | 0 |
| Titanium dioxide | 0 | 0 | 0.2 | 0 | 0 | 0 | 0 |
| Micronized titanium dioxide | 0 | 0 | 0 | 6 | 0 | 0 | 0 |
| Boron nitride (CaressnBN02 ex. Kobo) | 0 | 0 | 0 | 0 | 5 | 0 | 0 |
| Glycerol | 0 | 0 | 0 | 0 | 25 | 10 | 0 |
| Monolauroyl glyceride | 0 | 0 | 0 | 0 | 0 | 4 | 0 |
| Mss-500/20 | 0 | 0 | 0 | 0 | 0 | 0 | 0 |
| Self-assembled N-lauroyl-L-alanine polymer | 3 | 5 | 10 | 5 | 5 | 10 | 0 |
| Lauroyl alanine (containing 2% or more lauric acid) | 0 | 0 | 0 | 0 | 0 | 0 | 3 |

*The natural oil mixture contains 40% grape seed oil, 37.2% sunflower seed oil and 22.8% aloe oil.

The specific steps for preparing Formula 1 shown in Table 3 include: adding 57% of the natural oil mixture and 40% of the corn starch into a mixer and homogenizing to disperse the particles first. The particles in the oil dispersion were then heated to 83-86° C. while mixing. 3% lauroyl-L-alanine was added to the mixer while heating. The sample was heated and kept at 73-86° C. for 5-10 min. It was then cooled to a temperature between 65-72° C. while remaining mixable. The sample was then poured into a 30 ml tank to obtain the skin care composition, which was stored and used for evaluation. The skin care compositions of Formulae 2-6 were prepared using the same method as that for Formula 1, which will not be repeated here.

In the skin care compositions obtained according to the above examples, different types and amounts of particulate substances were added to the raw materials. As shown by the results, the addition of particulate substances increased the viscosity of the oil. In addition, the self-assembled N-lauroyl-L-alanine polymer helped to stably suspend the solid organic/inorganic particles or an oil-miscible liquid such as glycerol in the thickened natural oils to provide additional benefits to skin.

Four kinds of oil-insoluble particles, such as starch, TiO2, mica, boron nitride particles (Caress BN02 from Kobo) and an oil-miscible liquid such as glycerol were used. The same natural oil mixture, comprising 40% grape seed oil, 37.2% sunflower seed oil and 22.8% aloe oil, was used in Formulae 1-6. As shown by the results, the compositions obtained from all the formulae shown in Table 3 were stable at room temperature and in an oven at 48° C. with no separation of particles. In Formula 7 for comparison, lauroyl alanine (containing at least 2% lauric acid) was used instead of the self-assembled N-lauroyl-L-alanine polymer used in Formula 1. As a result, it was found that the resulting composition was unstable after 48 hours in an oven at 48° C., and oil emerged.

EXAMPLES 4-8

In these examples, the total weight parts of the amino acid toothpaste body are 100. The ingredients and specific contents thereof in the toothpastes are shown in Table 4:

TABLE 4

Ingredients and contents in the toothpastes

| | Amounts of starting materials | | | | |
|---|---|---|---|---|---|
| Starting materials | Example 4 | Example 5 | Example 6 | Example 7 | Example 8 |
| Sodium N-lauroyl-L-alanine polymer | 4.4 | 3 | 2 | 5 | 13.75 |

TABLE 4-continued

Ingredients and contents in the toothpastes

| Starting materials | Amounts of starting materials | | | | |
|---|---|---|---|---|---|
| | Example 4 | Example 5 | Example 6 | Example 7 | Example 8 |
| Carboxymethylcellulose | 4 | 6 | 4 | 6 | 3 |
| Hydrated silica | 35 | 35 | 33.4 | 35 | 33 |
| Water | 10 | 10 | 10 | 10 | 8 |
| Sorbitol | 37.5 | 35.5 | 35.5 | 33.5 | 32 |
| Glycerol | 5 | 6 | 6 | 6 | 5 |
| Polyglycol-400 | 2 | 2 | 2 | 2 | 3 |
| Edible essence | 1 | 1.5 | 1 | 1.5 | 1 |
| Chondrus Crispus carrageenan extract | 0.2 | 0.1 | 0.2 | 0.1 | 0.2 |
| Sodium saccharin | 0.2 | 0.2 | 0.2 | 0.2 | 0.2 |
| Sodium benzoate | 0.4 | 0.4 | 0.4 | 0.4 | 0.4 |
| Licorice extract | 0.1 | 0.1 | 0.1 | 0.1 | 0.15 |
| Purslane extract | 0.1 | 0.1 | 0.1 | 0.1 | 0.15 |
| CI42090 (brilliant blue aluminum lake) | 0.1 | 0.1 | 0.1 | 0.1 | 0.15 |

EXAMPLES 9-13

In these examples, the total weight parts of the amino acid toothpaste body are 100. The ingredients and specific contents thereof in the toothpastes are shown in Table 5:

TABLE 5

Ingredients and contents in the toothpastes

| Starting materials | Amounts of starting materials | | | | |
|---|---|---|---|---|---|
| | Example 9 | Example 10 | Example 11 | Example 12 | Example 13 |
| Sodium N-lauroyl-L-alanine polymer | 25 | 6 | 10 | 0.1 | 1 |
| Carboxymethylcellulose | 3 | 6 | 4 | 6 | 5 |
| Hydrated silica | 32 | 35 | 33.4 | 41.3 | 42 |
| Water | 5 | 10 | 10 | 10 | 9 |
| Sorbitol | 25.2 | 32.5 | 32.5 | 32.1 | 32.75 |
| Glycerol | 5 | 6 | 6 | 6 | 5 |
| Polyglycol-400 | 2 | 2 | 2 | 2 | 3 |
| Edible essence | 1.5 | 1.5 | 1 | 1.5 | 1 |
| Chondrus Crispus carrageenan extract | 0.2 | 0.1 | 0.2 | 0.1 | 0.2 |
| Sodium saccharin | 0.3 | 0.2 | 0.2 | 0.2 | 0.2 |
| Sodium benzoate | 0.4 | 0.4 | 0.4 | 0.4 | 0.4 |
| Licorice extract | 0.1 | 0.1 | 0.1 | 0.1 | 0.15 |
| Purslane extract | 0.15 | 0.1 | 0.1 | 0.1 | 0.15 |
| CI42090 | 0.15 | 0.1 | 0.1 | 0.1 | 0.15 |

The toothpaste according to the formula of Example 4 was prepared with the following specific steps: formulating an aqueous solution with 10 g water, 37.5 g sorbitol, 0.2 g sodium saccharin, 2 g polyethylene glycol-400, 5 g glycerol, 0.4 g sodium benzoate, and placing the aqueous solution in a paste making machine. Then, 4 g carboxymethyl cellulose, 35 g hydrated silica, 0.2 g Chondrus Crispus carrageenan extract, 0.1 g licorice extract and 0.1 g purslane extract were mixed, added to the paste making machine, stirred and ground for 20-30 minutes until the paste was uniform. Then, vacuum defoamation was performed. 4.4 g sodium N-lauroyl-L-alanine polymer, 1 g edible essence (mint flavor), and 0.1 g CI42090 were added in sequence to the paste making machine, stirred and ground for 10-15 minutes until the paste was uniform. Then, defoamation was performed to obtain the amino acid toothpaste. FIGS. 14-16 show the test reports of the amino acid toothpaste obtained according to the formula of Example 4 and the preparation method thereof. As can be seen from the report, the amino acid toothpaste provided according to the present disclosure is safe, and all tests meet the standards.

Examples 5-13 were all prepared using the method described in Example 4, which will not be repeated here.

According to the amounts in the formulae in Examples 4-13, amino acid toothpaste samples were prepared with different parts by weight of the amino acid surfactant by repeating the formulation tests several times. 100 volunteers with frequent toothache and gum bleeding were recruited to evaluate the effect. The frequency of use was once in the morning and once in the evening each day, the dosage was about 1 g paste per time, and the time for each brushing was about 5 minutes. As shown by the results, the toothpaste containing the amino acid surface active ingredient has obvious effects of analgesia, antiphlogosis and preventing gum bleeding. When evaluated from the two aspects of taste and deodorization, the weight percentage of the amino acid surface active ingredient in the toothpaste body is desirably 0.1-25%, preferably 0.5-10%, and most preferably 1-5%. When the amino acid surface active ingredient accounts for 1-5% by weight of the medicated toothpaste body, the pharmaceutical effect and taste of the toothpaste are in the best balance, and the removal of oral odor reaches the best level. At the same time, even if fruit is eaten immediately after teeth brushing, the taste of the fruit is not affected, and there is no feel of bitterness or aningeresting. FIGS. 17 and 18 compare the cleanness of a patent's teeth before and after cleaned with the amino acid toothpaste obtained according to Example 4 in the present disclosure. As can be seen from the figures, after brushed with the inventive amino acid toothpaste for a normal brushing time of 3 minutes, the patient's teeth are obviously whiter and cleaner than before.

Application Example 5 Application Example of Supramolecular Amino Acids in Laundry Liquid

TABLE 6

Supramolecular amino acid laundry liquid

| Components | Weight percentages of total for each components | |
|---|---|---|
| | Formulation 1 | Formulation 2 |
| Water | 78 | 78 |
| Self-assembled N-lauroyl-L-alanine polymer | 10 | 0 |
| Sodium hydroxide | 1.4 | 1.4 |
| Lauroyl alanine (containing 2% lauric acid) | 0 | 10 |
| Decyl glucoside | 5 | 5 |
| Cocamidopropyl betaine | 5 | 5 |
| GPL | 0.5 | 0.5 |
| DMDM | 0.1 | 0.1 |
| Fragrance | 0.05 | 0.05 |

The laundry liquid formulated in accordance with Formula 1 was tested by Suzhou Institute of Product Quality Supervision and Inspection, and the detergent power was higher than or equal to the detergent power of the standard laundry liquid. The resulting samples had a higher detergent power on JB01, JB02, and JB03 dirty cloth than the detergent power of the standard laundry liquid on JB01, JB02, JB03 dirty cloth. As tested by Suzhou Institute of Product Quality Supervision and Inspection, the laundry liquid formulated according to Formula 2 had a detergent power lower than that of the standard laundry liquid (FIG. 19).

Application Example 6 Application Example of Salt of Supramolecular Amino Acid and Basic Amino Acid in Facial Cleanser

TABLE 6

Supramolecular amino acid facial cleanser

| Components | Percentages of starting materials in the formula |
|---|---|
| Water | 82 |
| Self-assembled N-lauroyl-L-alanine polymer | 4 |
| Arginine | 0.7 |
| Cocamidopropyl betaine | 7.8 |
| Glycerol | 4.5 |
| Glutamic acid N,N-diacetate tetrasodium salt | 0.3 |
| GPL | 0.5 |
| DMDM | 0.1 |
| Fragrance | 0.05 |

The organic salt formed from the self-assembled N-lauroyl-L-alanine polymer and a basic amino acid (such as arginine) in an aqueous system is a clean surfactant. It is milder, non-irritating, and more suitable for sensitive skin. While the skin is cleaned, more care is provided to the skin.

Application Example 7 Application Example of Self-Assembled Polymer Formed From Self-Assembled Supramolecular Polymer and N-Lauroyl-L-Alanyl-L-Alanine in Laundry liquid

TABLE 7

Supramolecular amino acid laundry liquid

| Components | Percentages of starting materials in the formula |
|---|---|
| Water | 75.5 |
| Self-assembled N-lauroyl-L-alanine polymer | 8 |
| Self-assembled N-lauroyl-L-alanyl-L-alanine polymer | 2 |
| Sodium hydroxide | 1 |
| Cocamidopropyl betaine | 7.6 |
| Glycerol | 5 |
| Glutamic acid N,N-diacetate tetrasodium salt | 0.3 |
| GPL | 0.5 |
| DMDM | 0.1 |
| Fragrance | 0.05 |

The salt formed from the self-assembled N-lauroyl-L-alanine polymer and the self-assembled N-lauroyl-L-alanyl-L-alanine polymer under alkaline conditions is a clean surfactant. It is milder, does not hurt hands, and has a higher detergent power.

In addition, as can be understood by those skilled in the art, although some embodiments described herein include certain features included in other embodiments but not other features, combinations of features in different embodiments are intended to be included in the scope of the present disclosure, and form different embodiments. For example, in the following claims, any one of the claimed embodiments can be used in any combination.

What is claimed is:

1. A self-assembled amino acid supramolecular polymer or a salt thereof, wherein the polymer is formed by hydrogen bonding N-lauroyl-L-alanine monomers, wherein the salt thereof is formed by hydrogen bonding salt N-lauroyl-L-alanine monomers, wherein the polymer or the salt thereof is substantially free or free of lauric acid, and wherein the salt of the polymer has a solubility of no more than 15 g/100 ml in water; and the polymer has a melting point of 82-84° C.

2. The self-assembled amino acid supramolecular polymer or the salt thereof according to claim 1, wherein said hydrogen bonding N-lauroyl-L-alanine monomers provides a structure shown by Formula (I); or wherein said hydrogen bonding salt N-lauroyl-L-alanine monomers provides a structure shown by Formula (H):

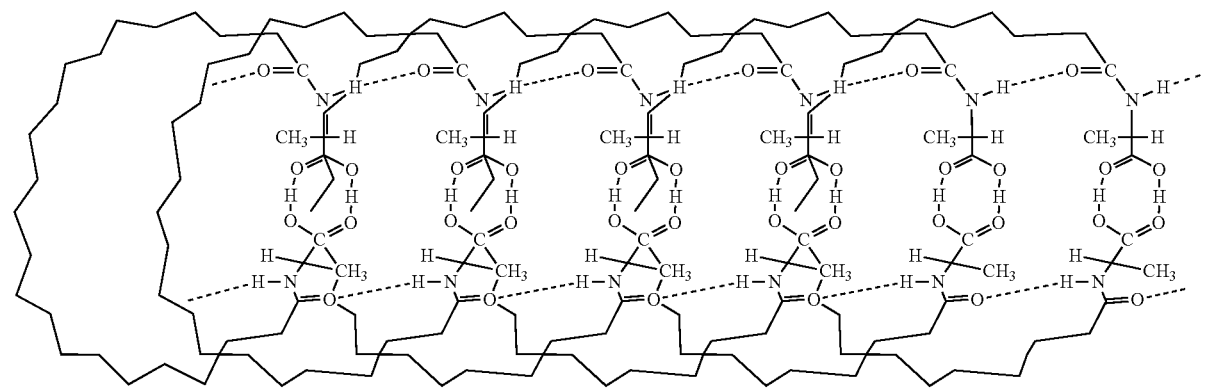
(I)
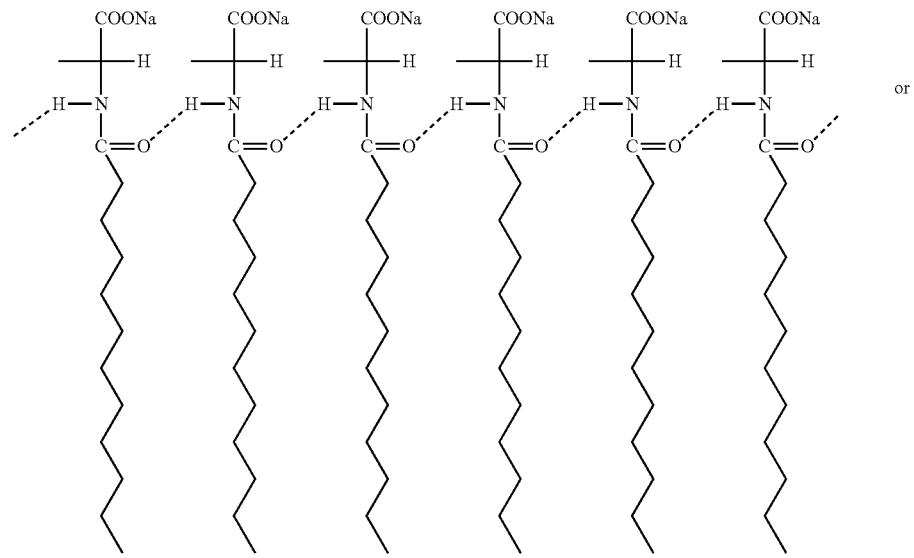
or
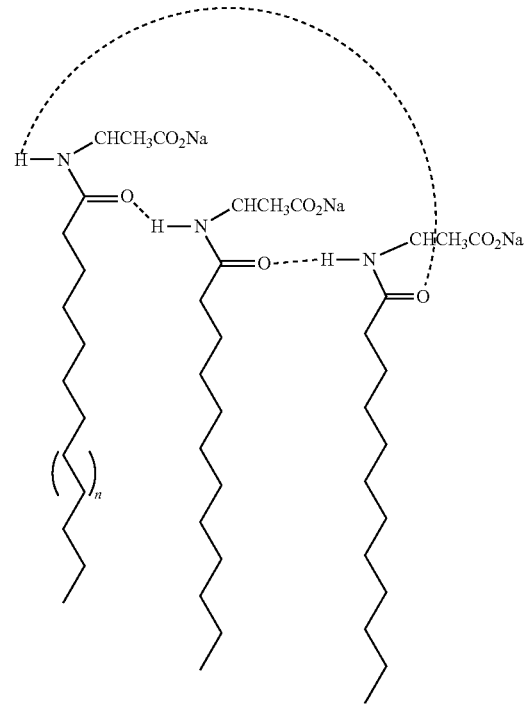
(II)

wherein n is 10-3000; and wherein an n number of sodium N-lauroyl-L-alanine molecules are linked in sequence by hydrogen bonds in the same plane, or an n number of sodium N-lauroyl-L-alanine molecules are linked in sequence by hydrogen bonds and the first and last molecules are also linked by hydrogen bonds to form a columnar structure.

3. The self-assembled amino acid supramolecular polymer or the salt thereof according to claim 1, wherein the polymer has a weight average molecular weight of between 2000 and 5,000,000; and wherein the salt of the polymer has a weight average molecular weight of between 2800 and 770,000.

4. A method for preparing the self-assembled amino acid supramolecular polymer or the salt thereof according to claim 1, wherein the method comprises the following steps:
    mixing a crude N-lauroyl-L-alanine product, a solvent, L-alanine and a catalyst and stirring to obtain the self-assembled amino acid supramolecular polymer or the salt thereof according to claim 1.

5. The method according to claim 4, wherein the crude N-lauroyl-L-alanine product is prepared with the following steps:
    (1) dissolving L-alanine and a metallic inorganic base in a mixed solution of distilled water and an organic solvent, and stirring uniformly to obtain an L-alanine salt solution;
    (2) adding lauroyl chloride and a metallic inorganic base to the L-alanine salt solution of (1), and stirring to obtain a pasty N-lauroyl-L-alanine salt;
    (3) acidifying the pasty N-lauroyl-L-alanine salt of (2) to precipitate a white solid gradually, and then placing the resultant in an ice bath, filtering to obtain the crude N-lauroyl-L-alanine product.

6. The method according to claim 5, wherein, in Step (1), a molar ratio of the L-alanine to the metallic inorganic base is 1:(1-1.5); the metallic inorganic base is selected from one or more of sodium hydroxide, potassium hydroxide, sodium carbonate, and potassium carbonate; and the organic solvent is selected from one or more of acetone, methanol, ethanol, acetonitrile, and tetrahydrofuran.

7. The method according to claim 5, wherein, in Step (2), a feeding molar ratio of the lauroyl chloride to the L-alanine is (0.8-1):1; the stirring is conducted under the following conditions: temperature 5-50° C., time 0.5-3.5 h; the metallic inorganic base has a concentration of 30-80%; and the metallic inorganic base is selected from one or more of sodium hydroxide, potassium hydroxide, sodium carbonate, and potassium carbonate.

8. The method according to claim 4, wherein the solvent is selected from acetone, methanol, ethanol, acetonitrile, tetrahydrofuran, and a mixed solvent comprising one or more of the above solvents and water; the catalyst is selected from one or more of sulfuric acid, p-toluenesulfonic acid, and an emulsifier; a molar ratio of the crude N-lauroyl-L-alanine product, the solvent, L-alanine, and the catalyst is 1:(5-10):(0.2-1.1): (0.001-0.2); and the stirring is conducted under the following conditions: temperature 125-100° C., pressure 5 kg-50 kg, time 1-3 h.

9. A surfactant comprising the self-assembled amino acid supramolecular polymer or the salt thereof according to claim 1.

10. The surfactant according to claim 9, wherein the surfactant is suitable for use in the field of daily chemicals, agriculture and pharmaceutical industry, or combination thereof.

11. A composition comprising (i) the self-assembled amino acid supramolecular polymer or the salt thereof according to claim 1, and (ii) a polymer formed by hydrogen bonding N-lauroyl-L-alanyl-L-alanine monomers or a salt thereof, wherein the polymer formed by hydrogen bonding N-lauroyl-L-alanyl-L-alanine monomers or the salt thereof is 0-40 wt. % based on the total weight of the composition.

12. An amino acid toothpaste comprising a friction agent, a humectant, a thickener and a surfactant, wherein the surfactant comprises the self-assembled amino acid supramolecular polymer or the salt thereof according to claim 1; wherein the toothpaste comprises 0.1-25 w/w % of the surfactant, 10-50 w/w % of the friction agent, 5-40 w/w % of the humectant, and 0.1-6 w/w % of the thickener, based on a total weight of the toothpaste.

13. A skin care composition comprising, based on total weight of the composition:

| | |
|---|---|
| Oil | 50-95% by weight |
| Surfactant | 0.5-30% by weight |
| Suspended particles | 0-45% by weight | wherein the surfactant comprises an amino acid surfactant that comprises the self-assembled amino acid supramolecular polymer or the salt thereof according to claim 1.

14. An amino acid laundry liquid comprising a surfactant, a softener, a chelating agent, deionized water, a preservative and a fragrance, wherein weight percentages of these components in the amino acid laundry liquid are:

| | |
|---|---|
| Surfactant | 5-50%, |
| Softener | 0.1-3%, |
| Chelating agent | 0.1-5%, |
| Deionized water | 50-90%, |
| Preservative | 0.1-6%, |
| Fragrance | 0.1-2%, | wherein the surfactant comprises an amino acid surfactant that comprises the self-assembled amino acid supramolecular polymer or the salt thereof according to claim 1.

15. An amino acid perfumed soap comprising a surfactant, a fatty acid, glycerol, a softener, a chelating agent, a filler, and deionized water, wherein weight percentages of these components in the amino acid perfumed soap are:

| | |
|---|---|
| Surfactant | 10-50%, |
| Fatty acid | 0.1-7%, |
| Glycerol | 0.1-5%, |
| Softener | 0.1-6%, |
| Chelating agent | 0.1-1%, |
| Filler | 10-40%, |
| Deionized water | 1-5%, | wherein the surfactant comprises an amino acid surfactant that comprises the self-assembled amino acid supramolecular polymer or the salt thereof according to claim 1.

16. An amino acid laundry powder comprising a surfactant and a friction agent, wherein weight percentages of these components in the amino acid laundry powder are:

| | |
|---|---|
| Surfactant | 10-50%, |
| Friction agent | 50-90%, | wherein the surfactant comprises an amino acid surfactant that comprises the self-assembled amino acid supramolecular polymer or the salt thereof according to claim 1.

17. An amino acid cleanser essence comprising a surfactant, deionized water, a thickener, glycerol, a preservative and a fragrance, wherein weight percentages of these components in the amino acid cleanser essence are:

| | |
|---|---|
| Surfactant | 5-20%, |
| Deionized water | 70-90%, |
| Thickener | 1-2% |
| Glycerol | 5-10% |
| Preservative | 0.1-6% |
| Fragrance | 0.1-2%, | wherein the surfactant comprises an amino acid surfactant that comprises the self-assembled amino acid supramolecular polymer or the salt thereof according to claim 1.

18. An amino acid facial mask comprising a surfactant, deionized water, glycerol, a preservative and a fragrance, wherein weight percentages of these components in the amino acid facial mask are:

| | |
|---|---|
| Surfactant | 0.1-5%, |
| Deionized water | 50-90%, |
| Glycerol | 1-10%, |
| Preservative | 0.1-2% |
| Fragrance | 0.1-2%, | wherein the surfactant comprises an amino acid surfactant that comprises the self-assembled amino acid supramolecular polymer or the salt thereof according to claim 1.

* * * * *

UNITED STATES PATENT AND TRADEMARK OFFICE
CERTIFICATE OF CORRECTION

PATENT NO. : 11,566,110 B2
APPLICATION NO. : 16/972461
DATED : January 31, 2023
INVENTOR(S) : Jian Zhang Page 1 of 2

It is certified that error appears in the above-identified patent and that said Letters Patent is hereby corrected as shown below:

In the Specification

At Column 1-2, Lines 41-58; Column 9, Lines 25-44:
Please replace the structure of formula (I) with the following structure:

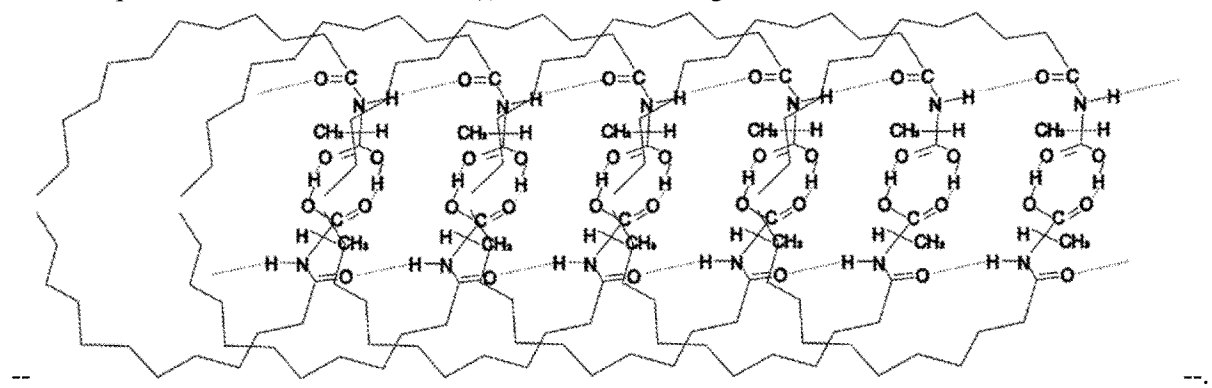

At Column 13-14, Lines 4-32:
Please replace the structure of formula (I') with the following structure:

Signed and Sealed this
Twenty-second Day of August, 2023

Katherine Kelly Vidal
*Director of the United States Patent and Trademark Office*

CERTIFICATE OF CORRECTION (continued)
U.S. Pat. No. 11,566,110 B2

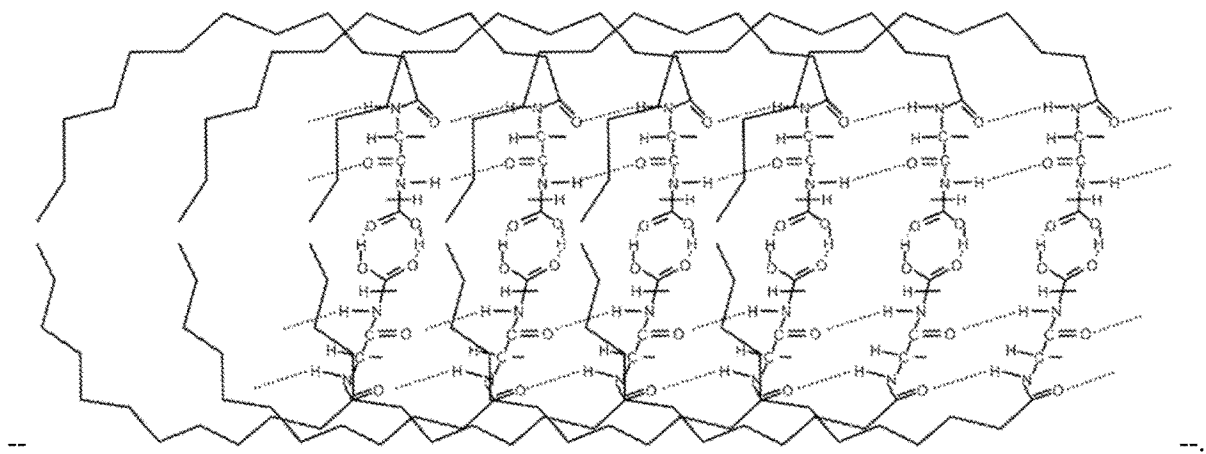

--                                                                          --.

In the Claims

Claim 2 at Column 32, Line 67:
Please replace the term "Formula H" with --Formula (II)--.

Claim 2 at Column 33-34:
Please replace the structure of formula (I) with the following structure:

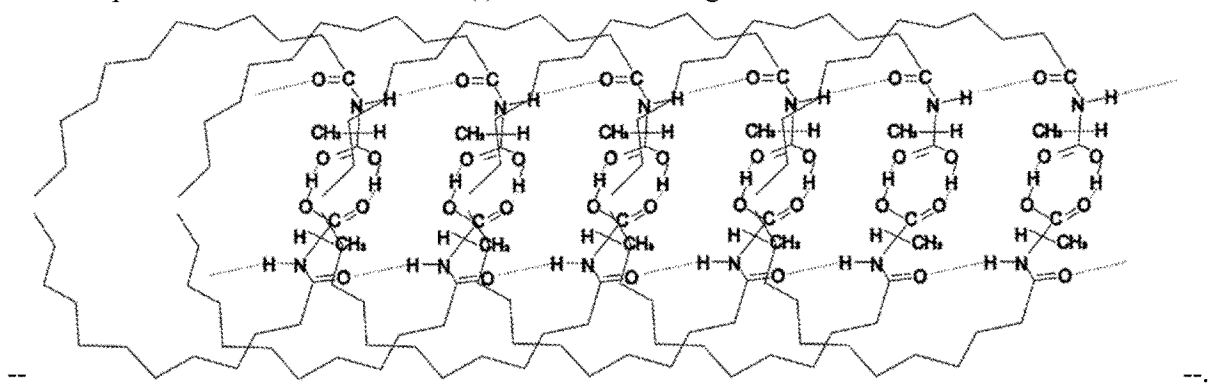

--                                                                          --.